US010420909B2

(12) United States Patent
Martin et al.

(10) Patent No.: US 10,420,909 B2
(45) Date of Patent: Sep. 24, 2019

(54) APPARATUS FOR CONTROLLING PRESSURIZED GAS DELIVERED TO A PATIENT

(71) Applicant: ResMed Pty Ltd, Bella Vista, New South Wales (AU)

(72) Inventors: Dion Charles Chewe Martin, Sydney (AU); Etienne Veschambre, Sydney (AU); Paul Jan Klasek, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 853 days.

(21) Appl. No.: 14/776,960

(22) PCT Filed: Mar. 14, 2014

(86) PCT No.: PCT/AU2014/000280
§ 371 (c)(1),
(2) Date: Sep. 15, 2015

(87) PCT Pub. No.: WO2014/138820
PCT Pub. Date: Sep. 18, 2014

(65) Prior Publication Data
US 2016/0022948 A1 Jan. 28, 2016

Related U.S. Application Data

(60) Provisional application No. 61/791,620, filed on Mar. 15, 2013.

(51) Int. Cl.
*A61M 16/00* (2006.01)
*A61M 16/08* (2006.01)
(Continued)

(52) U.S. Cl.
CPC ........ *A61M 16/0875* (2013.01); *A61M 16/06* (2013.01); *A61M 16/0605* (2014.02);
(Continued)

(58) Field of Classification Search
CPC .......... A61M 16/0875; A61M 16/0683; A61M 16/0666; A61M 16/0605; A61M 16/0672;
(Continued)

(56) References Cited

U.S. PATENT DOCUMENTS

| 4,007,737 A | 2/1977 | Paluch |
| 4,269,183 A | 5/1981 | Hunt |

(Continued)

FOREIGN PATENT DOCUMENTS

| GB | 2 053 694 | 2/1981 |
| WO | WO 2002/015969 | 2/2002 |
| WO | WO 2013/067592 | 5/2013 |

OTHER PUBLICATIONS

First Examination Report issued in related New Zealand Application No. 631169 dated Oct. 29, 2015, 2 pages.
(Continued)

*Primary Examiner* — Steven O Douglas
(74) *Attorney, Agent, or Firm* — Nixon & Vanderhye P.C.

(57) ABSTRACT

A mask assembly for delivering pressurized gas to a patient comprising a mask having an inspiratory port and an expiratory port located on generally opposite sides, wherein said ports are sized, oriented, positioned, and/or spaced apart a sufficient distance to allow a cross-flow of pressurized gas to flow through the mask assembly; an outlet limb connected to the expiratory port and having an aperture in pneumatic communication with the breathing chamber; the aperture size being variable between a first, open configuration and at least one second configuration that is different from the first. A ventilation system for delivering pressurized gas to a patient comprising a seal formed with the patient's airways and in pneumatic communication with a plenum chamber; an exchanger positioned at least partially within the plenum chamber, and in pneumatic communication with inspiratory and expiratory flow paths, to recover heat and/or moisture from gas exhaled by the patient.

28 Claims, 20 Drawing Sheets

(51) Int. Cl.
*A61M 16/06* (2006.01)
*A61M 16/10* (2006.01)
*A61M 16/16* (2006.01)

(52) U.S. Cl.
CPC .... *A61M 16/0666* (2013.01); *A61M 16/0672* (2014.02); *A61M 16/0683* (2013.01); *A61M 16/0833* (2014.02); *A61M 16/1045* (2013.01); *A61M 16/16* (2013.01); *A61M 2210/0618* (2013.01)

(58) Field of Classification Search
CPC .. A61M 16/06; A61M 16/16; A61M 16/1045; A61M 16/0833; A61M 2210/0618
See application file for complete search history.

(56) References Cited

U.S. PATENT DOCUMENTS

| | | | | |
|---|---|---|---|---|
| 4,412,537 A | * | 11/1983 | Tiger | A61M 16/1075 128/204.17 |
| 4,454,880 A | * | 6/1984 | Muto | A61M 16/06 128/205.25 |
| 4,593,688 A | * | 6/1986 | Payton | A61M 16/06 128/200.28 |
| 4,676,239 A | | 6/1987 | Humphrey | |
| 4,944,310 A | * | 7/1990 | Sullivan | A61M 16/00 128/205.25 |
| 5,050,593 A | | 9/1991 | Poon | |
| 5,109,839 A | * | 5/1992 | Blasdell | A61M 16/06 128/203.12 |
| 5,896,857 A | * | 4/1999 | Hely | A62B 9/02 128/203.11 |
| 6,019,101 A | | 2/2000 | Cotner | |
| 6,095,140 A | * | 8/2000 | Poon | A61M 16/08 128/204.18 |
| 6,792,623 B2 | | 9/2004 | Luppi | |
| 8,517,017 B2 | * | 8/2013 | Bowditch | A61M 16/00 128/204.23 |
| 8,844,530 B2 | * | 9/2014 | Birnkrant | A61M 1/0023 128/204.21 |
| 9,649,458 B2 | * | 5/2017 | Andrieux | A61M 16/0051 |
| 9,656,037 B2 | * | 5/2017 | Guyette | A61M 16/06 |
| 2003/0145859 A1 | * | 8/2003 | Bohn | A61M 16/06 128/206.24 |
| 2009/0032018 A1 | | 2/2009 | Eaton et al. | |
| 2012/0304985 A1 | | 12/2012 | Lalonde | |

OTHER PUBLICATIONS

International Search Report for PCT/AU2014/000280 dated Jun. 10, 2014, eight (8) pages.
Written Opinion of the ISA for PCT/AU2014/000280 dated Jun. 10, 2014, nine (9) pages.
Written Opinion of the ISA for PCT/AU2014/000280 dated Mar. 23, 2015, nine (9) pages.
International Preliminary Report on Patentability for PCT/AU2014/000280 dated Jul. 6, 2015, 21 pages.
Further Examination Report issued in related New Zealand Application No. 631169 dated Mar. 22, 2016, 2 pages.

* cited by examiner

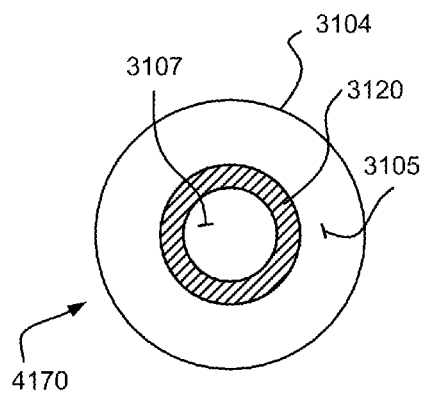
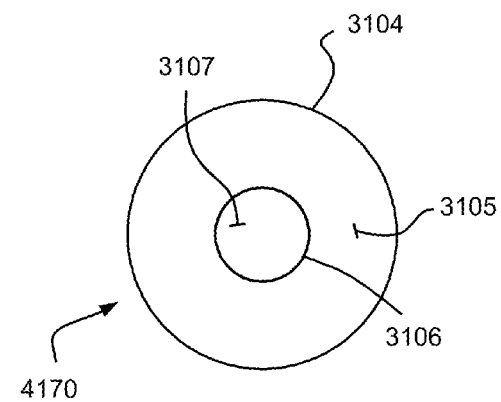
FIG. 12a    FIG. 12b
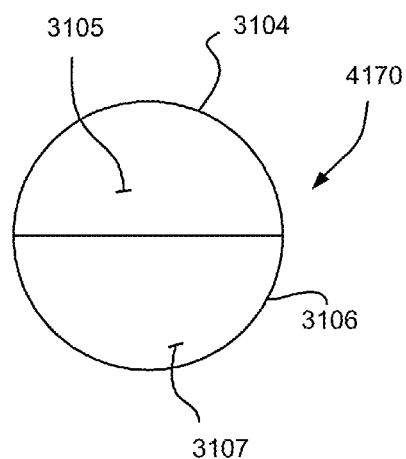
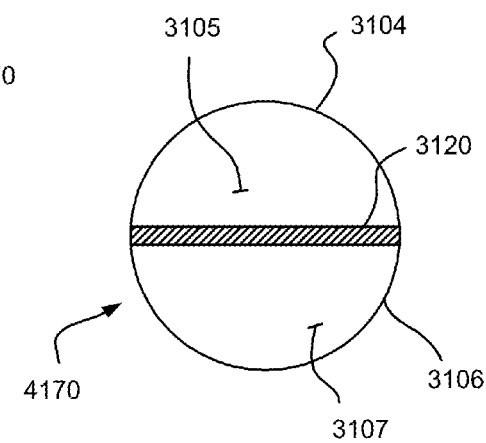
FIG. 12c    FIG. 12d

APPARATUS FOR CONTROLLING PRESSURIZED GAS DELIVERED TO A PATIENT

1 CROSS-REFERENCE TO RELATED APPLICATIONS

This application is the U.S. national phase of International Application No. PCT/AU2014/000280 filed Mar. 14, 2014 which designated the U.S. and claims the benefit of U.S. Provisional Application No. 61/791,620, filed Mar. 15, 2013, the entire contents of each of which are hereby incorporated by reference.

2 BACKGROUND OF THE TECHNOLOGY

2.1 Field of the Technology

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

2.2 Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnoea, repeated chest infections, morning headaches, fatigue, poor sleep quality and loss of appetite.

Otherwise healthy individuals may take advantage of systems and devices to prevent respiratory disorders from arising.

2.2.1 Systems

Known products used for treating respiratory breathing disorders are the S9, Stellar and Elisee Therapy Systems, all manufactured by ResMed.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

2.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

2.2.3.1 Seal-Forming Portion

Patient interfaces typically include a seal-forming portion.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

2.2.3.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

2.2.3.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner of the patient, e.g. through noise or focussed airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2:2007, 10 cm $H_2O$ pressure at 1 m)

| Mask name | Mask type | A-weighted sound power level dbA (uncertainty) | A-weighted sound pressure dbA (uncertainty) | Year (approx.) |
| --- | --- | --- | --- | --- |
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |
| ResMed Mirage series I, II (*) | full face | 31.7 | 23.7 | 2000 |
| ResMed UltraMirage | full face | 35 (3) | 27 (3) | 2004 |
| ResMed Mirage Quattro | full face | 26 (3) | 18 (3) | 2006 |
| ResMed Mirage Quattro FX | full face | 27 (3) | 19 (3) | 2008 |

(* one specimen only, measured using test method specified in ISO3744 in CPAP mode at 10 cm$H_2O$)

Sound pressure values of a variety of objects are listed below

| Object | A-weighted sound pressure dbA (uncertainty) | Notes |
| --- | --- | --- |
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.4 Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063, 328 and WO 2006/130,903 (describing amongst other things aspects of ResMed LIBERTY full-face mask); International Patent Application WO 2009/052,560 (describing amongst other things aspects of ResMed SWIFT FX nasal pillows).

3 (B) BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, treatment or prevention of a respiratory disorder.

Another aspect of the present technology relates to methods used in the diagnosis, treatment or prevention of a respiratory disorder.

One form of the present technology comprises a patient interface system, ventilation system, and method for ventilating a patient that overcomes the shortcomings of the prior art.

Another aspect of the present technology is directed to a patient interface system for delivering pressurized gas to a patient. The patient interface system may comprise a patient interface having an inspiratory port and an expiratory port located on generally opposite sides of a breathing chamber, wherein said inspiratory port and said expiratory port are sized, oriented, positioned, and/or spaced apart a sufficient distance to allow a cross-flow of pressurized gas to flow through the breathing chamber; and an outlet limb connected to the expiratory port, said outlet limb having an aperture in pneumatic communication with the breathing chamber, said aperture having an aperture size that is variable between a first configuration that is open and at least one second configuration that is different from the first configuration.

In examples, (a) the patient interface system may be arranged for delivering pressurized gas to a pediatric patient, (b) the patient interface system may further comprise headgear to removably attach the patient interface to the face of the patient, (c) the patient interface may further comprise a cushion adapted to contact the skin of the patient, (d) the patient interface may comprise a nasal mask, (e) the patient interface may comprise a full-face mask, (f) the outlet limb may comprise a controllable valve, (g) the controllable valve may be adapted to release pressurized gas from the outlet limb through the aperture to atmosphere in the first configuration, (h) the controllable valve may be adapted to prevent the release of pressurized gas from the outlet limb through the aperture to atmosphere in the second configuration, (i) the patient interface may define a substantially pneumatically unobstructed path from the inspiratory port, through the breathing chamber and to the expiratory port, (j) the path may be substantially linear, (k) the patient interface system may further comprise an inlet limb having a first end connected to the inspiratory port and adapted to connect to a flow generator at a second end, (l) the inspiratory port and the expiratory port may be substantially coaxial, (m) the patient interface may comprise a non-vented patient interface, (n) the inspiratory port and the expiratory port may be disposed on the patient interface such that pressurized gas flows unidirectionally therethrough, and/or (o) the inspiratory port and the expiratory port may be disposed on the patient interface such that there is substantially no backflow through the inspiratory port.

Another aspect of the present technology may be directed to a patient interface system for delivering breathable gas to a patient. The patient interface system may comprise a gas chamber formed, at least in part, by a patient interface; an inspiratory flow path connected to a first side of the gas chamber; and an expiratory flow path connected to a second side of the gas chamber, said second side being disposed generally opposite the first side, the expiratory flow path having an opening disposed at a distance from the gas chamber, said opening having an opening size that is variable between a first open configuration and at least one second configuration that is different from the first configuration.

In examples, (a) the patient interface system may be arranged for delivering pressurized gas to a pediatric patient, (b) the patient interface may further comprise a cushion adapted to contact the face of the patient, (c) the patient interface system may further comprise headgear adapted to secure the patient interface system to the patient, (d) said inspiratory flow path may comprise an inlet limb and said expiratory flow path may comprise an outlet limb, and said inlet limb and said outlet limb may be sized, oriented, positioned, and/or spaced apart a sufficient distance to allow a cross-flow of pressurized gas to flow through the gas chamber (e) the patient interface may form a substantially pneumatically unobstructed path from the inspiratory flow path to the expiratory flow path, (f) the inspiratory flow path and the expiratory flow path may be in pneumatic communication such that there is substantially no backflow through the inspiratory flow path, (g) the inspiratory flow path and the expiratory flow path may he designed to provide a substantially unidirectional flow of gas from the inspiratory flow path through the gas chamber and to the expiratory flow path, (h) the substantially unidirectional flow of gas may be along a substantially linear path, (i) the patient interface may comprise a nasal mask, (j) the patient interface may comprise a full-face mask, and/or (k) the patient interface may comprise a non-vented patient interface.

Another aspect of the present technology may be directed to a method for ventilating a patient with a ventilation system having a patient interface, an inlet limb and an outlet limb distinct from the inlet limb, the limbs being pneumatically connected to the patient interface at opposite sides, and a controllable valve. The method may comprise providing a flow of pressurized, breathable gas to the patient; and detecting whether the patient is inspiring or expiring; wherein when the patient is inspiring, closing the outlet limb from atmosphere and providing a primary flow to the patient interface through the inlet limb, and wherein when the patient is expiring, opening the outlet limb to atmosphere and providing a bias flow through the inlet limb, through the patient interface, and to the outlet limb.

In examples, (a) the patient is a pediatric patient, (b) the method may further comprise insufflating the patient with the primary flow, and/or (c) the patient interface, at least partly, may form a gas chamber, and the method may further comprise flushing exhaled gas from the gas chamber and the outlet limb to atmosphere with the bias flow by opening a controllable valve, a controllable opening, or an actuator positioned to be in pneumatic communication with the bias flow through the outlet limb.

Another aspect of the present technology may be directed to a ventilation system for ventilating a patient. The ventilation system may comprise a flow generator to generate a flow of breathable gas; a non-vented patient interface having an inlet port and an outlet port generally opposite of the inlet port; an inlet limb pneumatically connected to the patient interface at the inlet port; an outlet limb pneumatically connected to the patient interface at the outlet port; a controllable valve attached to the outlet limb and variable between a closed position and an open position; a controller to control the flow generator and the controllable valve; and a continuous flow path formed by the inlet limb, the non-vented patient interface, and the outlet limb, wherein when the controllable valve is in the open position the flow of breathable gas generated flows through and out of the flow path, and when the controllable valve is in the closed position the flow of breathable gas flows into the respiratory system of the patient.

In examples, (a) the patient interface system may be arranged for delivering pressurized gas to a pediatric patient, (b) the ventilation system may further comprise at least one sensor for detecting whether patient is inspiring or expiring, (c) the ventilation system may further comprise a cushion adapted to contact the face of the patient, (d) the ventilation system may further comprise headgear adapted to releasably attach at least the patient interface to the patient, (e) the inlet port and the outlet port may be disposed on the patient interface such that there is substantially no backflow through the inlet port, (f) the inlet port and the outlet port may be disposed on the patient interface in a cross-flow configuration, (g) the inlet limb and the outlet limb may be designed to provide a substantially unidirectional flow of gas from the inlet port through the patient interface to the outlet port, (h) the substantially unidirectional flow of gas may be along a substantially linear path, (i) the patient interface may comprise a nasal mask, (h) the patient interface may comprise a full-face mask, (i) the inlet limb and the outlet limb may be pneumatically connected to the patient interface such that the gas enters and exits the patient interface through opposite sides, (j) when the controllable valve is in the open position the flow of breathable gas generated by the flow generator is adapted to flush the patient's exhaled gas from the patient interface, (k) gas discharged through the controllable valve may be discharged to atmosphere, and/or (l) the inlet port and the outlet port may be substantially coaxial.

Another aspect of the present technology is directed to a ventilation system to provide a flow of pressurized breathable gas to a patient via the patient's airways. The ventilation system may comprise: a patient interface having a seal-forming structure to form a seal with an entrance to the patient's airways and a plenum chamber in pneumatic communication with the seal-forming structure; a conduit having an inspiratory flow path and an expiratory flow path, the conduit connected to the patient interface at a first end; and an exchanger configured to recover heat and/or moisture from gas exhaled by the patient, the exchanger positioned within the plenum chamber to be in pneumatic communication with the inspiratory flow path and the expiratory flow path.

In examples, (a) the :inspiratory flow path and the expiratory flow path may be arranged coaxially within the conduit, (b) the expiratory flow path may be positioned internally to the inspiratory flow path, (c) the inspiratory flow path and the expiratory flow path may be arranged parallel and adjacent to one another, (d) the exchanger may be positioned within the plenum chamber such that each section of the plenum chamber is either substantially a part of the inspiratory flow path or substantially a part of the expiratory flow path, or is substantially exposed to a cross airflow between the inspiratory flow path and the expiratory flow path to expel exhaled gas of the patient from the plenum chamber; (e) the exchanger may comprise a gas impermeable material (f) the exchanger may be positioned within the plenum chamber to allow exhaled gas from the patient's airways to reach the expiratory flow path without passing through a wall of the exchanger, (g) the exchanger may be positioned within the plenum chamber such that exhaled gas from the patient's airways only reaches the expiratory flow path by passing through the exchange, (h) the exchanger may comprise a gas permeable material, (i) the exchanger may comprise a moisture permeable and/or heat conductive material, (j) the conduit may comprise a heater and/or thermal insulation, (k) shared walls of the inspiratory flow path and the expiratory flow path may comprise a gas impermeable material that is moisture permeable and/or thermally conductive, and/or (l) the inspiratory flow path and the expiratory flow path may be contained within an external wall of the conduit.

Another aspect of one form of the present technology is a patient interface that is moulded or otherwise constructed with a clearly defined perimeter shape which is intended to match that of an intended wearer.

Of course, portions of the examples or aspects may form sub-aspects or sub-examples of the present technology. Also, various ones of the examples, sub-aspects and/or aspects may be combined in various manners and also constitute additional examples, sub-examples, aspects or sub-aspects of the present technology.

Other features of the technology will be apparent from consideration of the information contained in the following detailed description, abstract, drawings and claims.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system in accordance with the present technology. A patient 1000 wearing a patient interface 3000, receives a supply of air at positive pressure from a PAP device or flow generator 4000. Air from the PAP device is humidified in a humidifier 5000, and passes along a conduit 4170 to the patient 1000. A bed partner 1100 is also shown.

4.2 Therapy 4.2.1 Respiratory System

4.2.2 Facial Anatomy

Figure 2A:
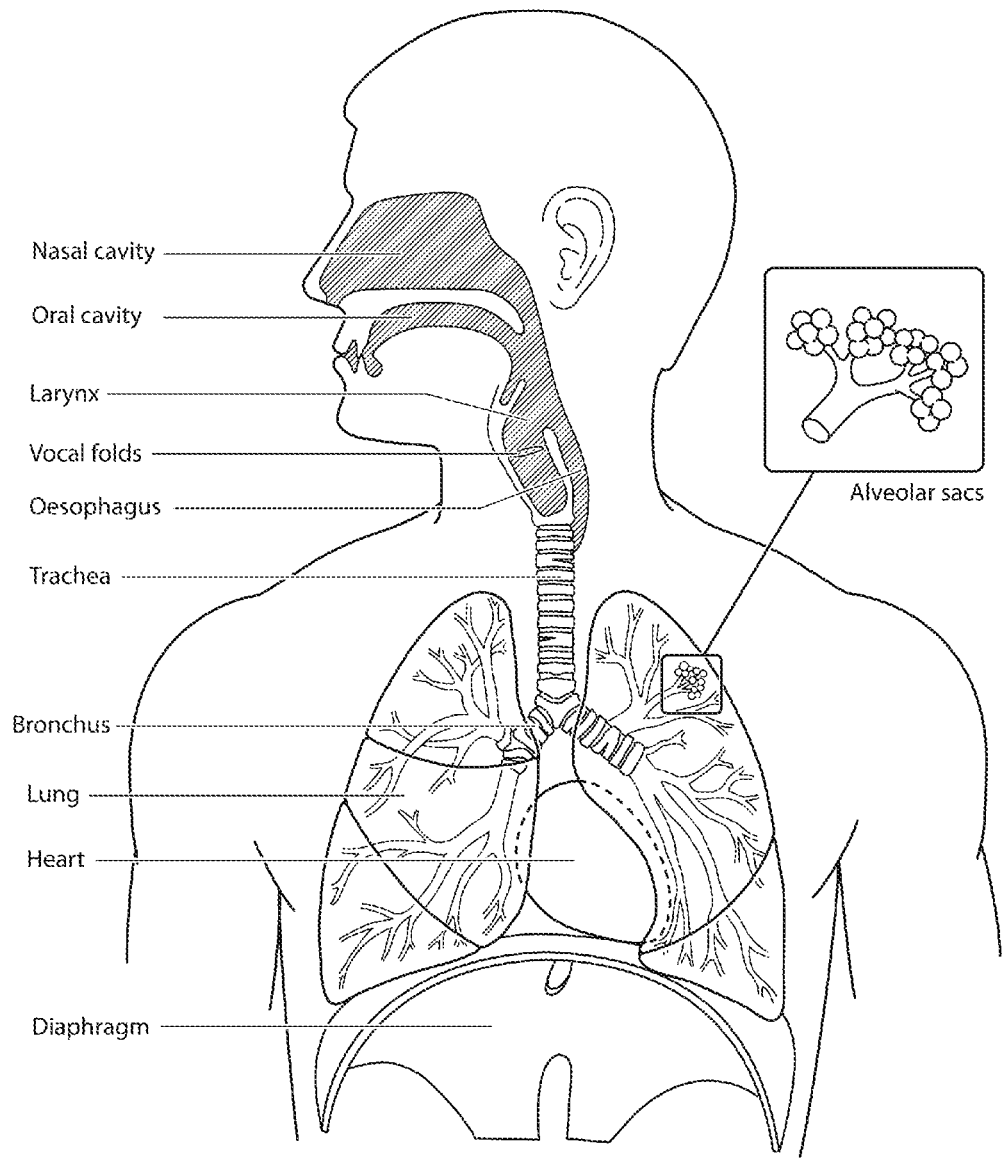
FIG. 2a shows an overview of a human respiratory system including the nasal and oral cavities, the larynx, vocal folds, oesophagus, trachea, bronchus, lung, alveolar sacs, heart and diaphragm.
Figure 2B:
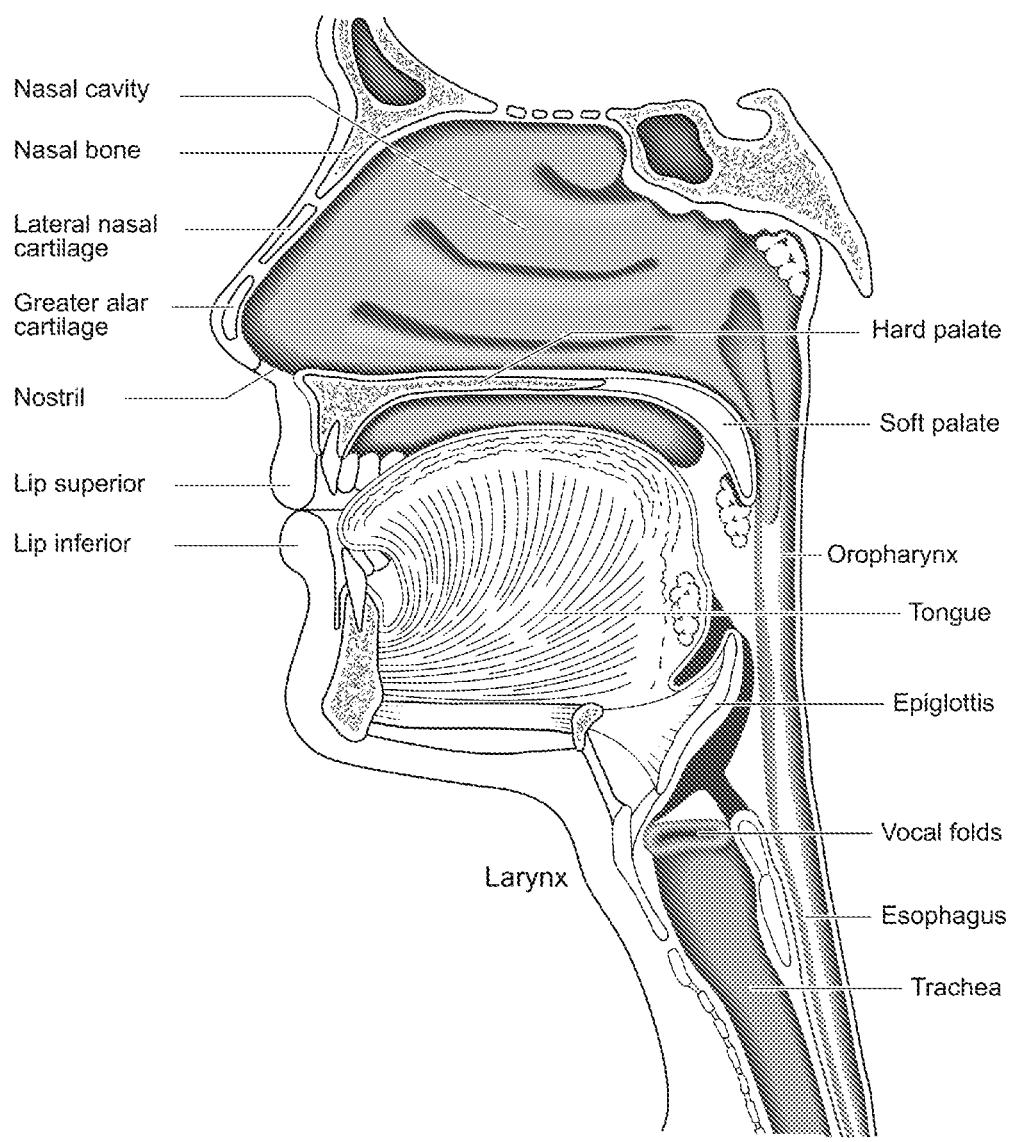
FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
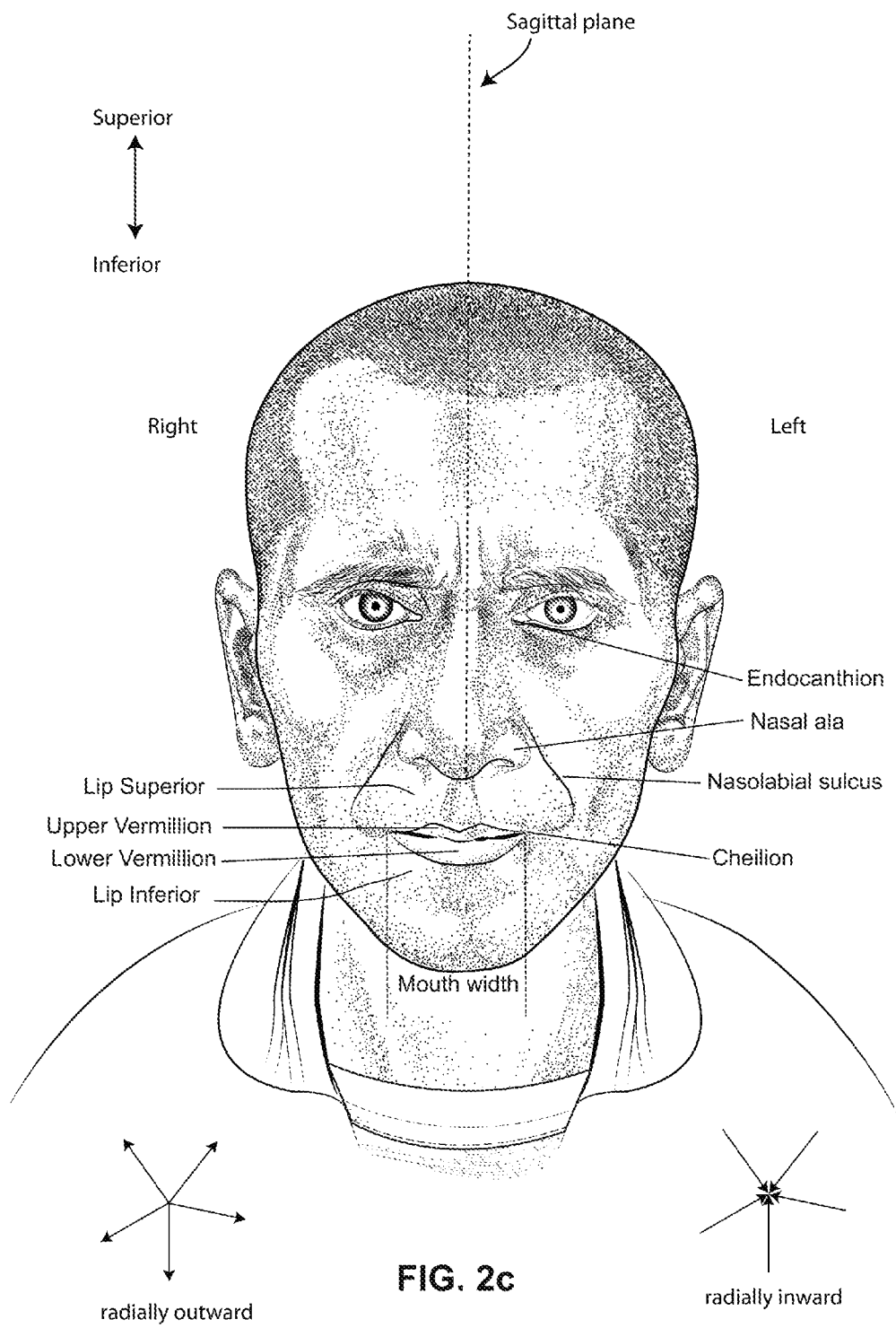

FIG. 2c is a front view of a face with several features of surface anatomy identified including the lip superior, upper vermillion, lower vermillion, lip inferior, mouth width, endocanthion, a nasal ala, nasolabial sulcus and cheilion.

Figure 2D:
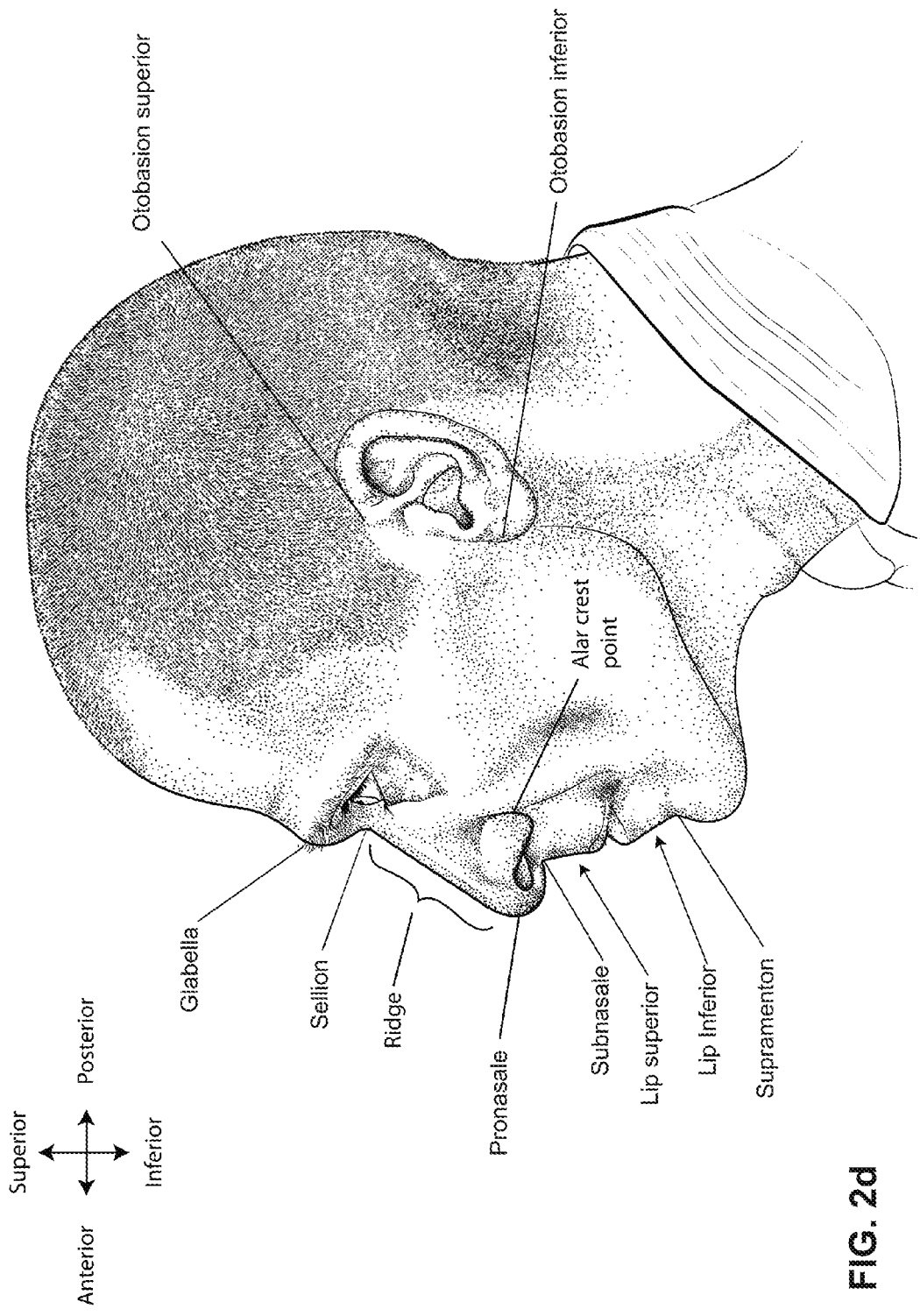

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

Figure 2E:
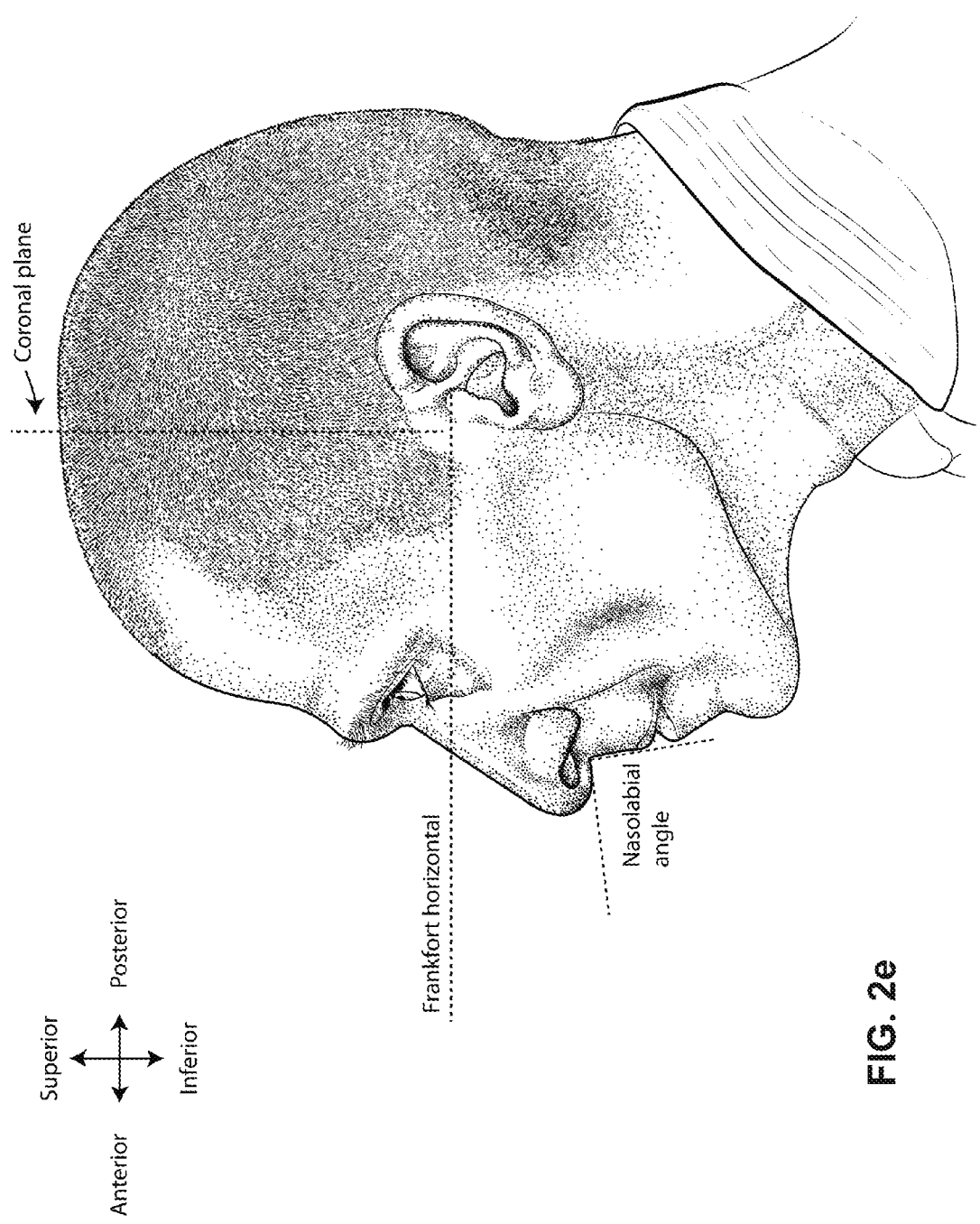

FIG. 2e is a further side view of a head. The approximate locations of the Frankfort horizontal and nasolabial angle are indicated.

Figure 2F:
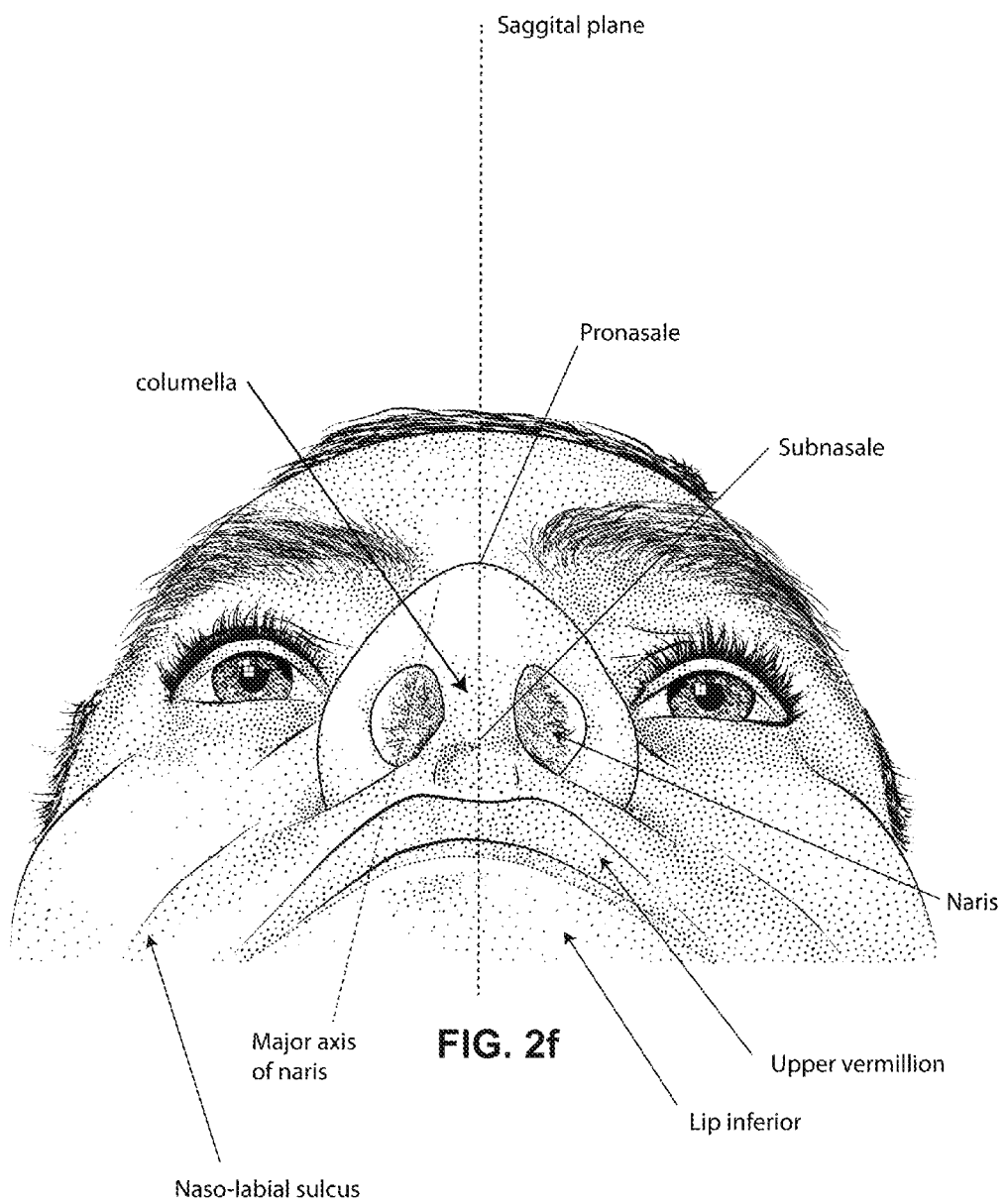

FIG. 2f shows a base view of a nose.

Figure 2I:
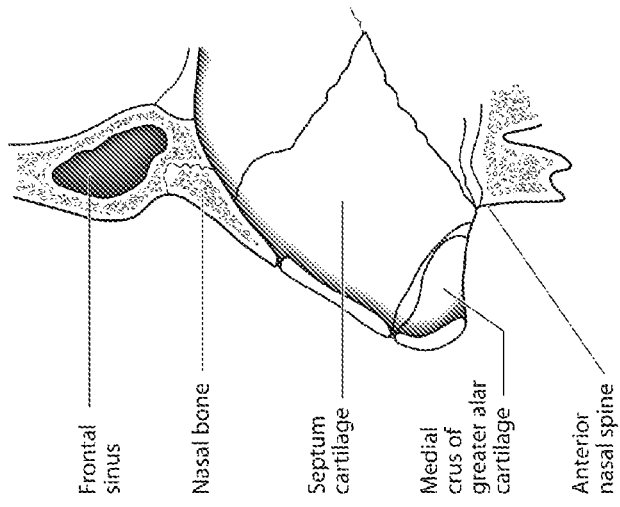
Figure 2H:
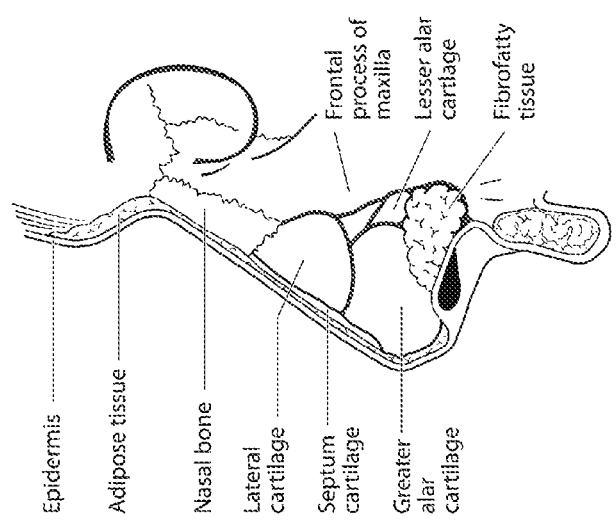
Figure 2G:
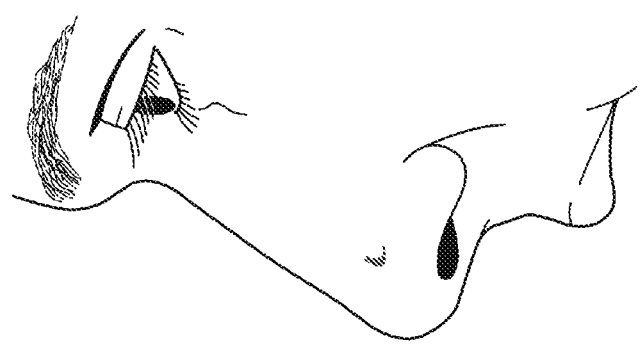

FIG. 2g shows a side view of the superficial features of a nose.

FIG. 2h shows subcutaneal structures of the nose, including lateral cartilage, septum cartilage, greater alar cartilage, lesser alar cartilage and fibrofatty tissue.

FIG. 2i shows a medial dissection of a nose, approximately several millimeters from a sagittal plane, amongst other things showing the septum cartilage and medial crus of greater alar cartilage.

Figures 2J, 2K:
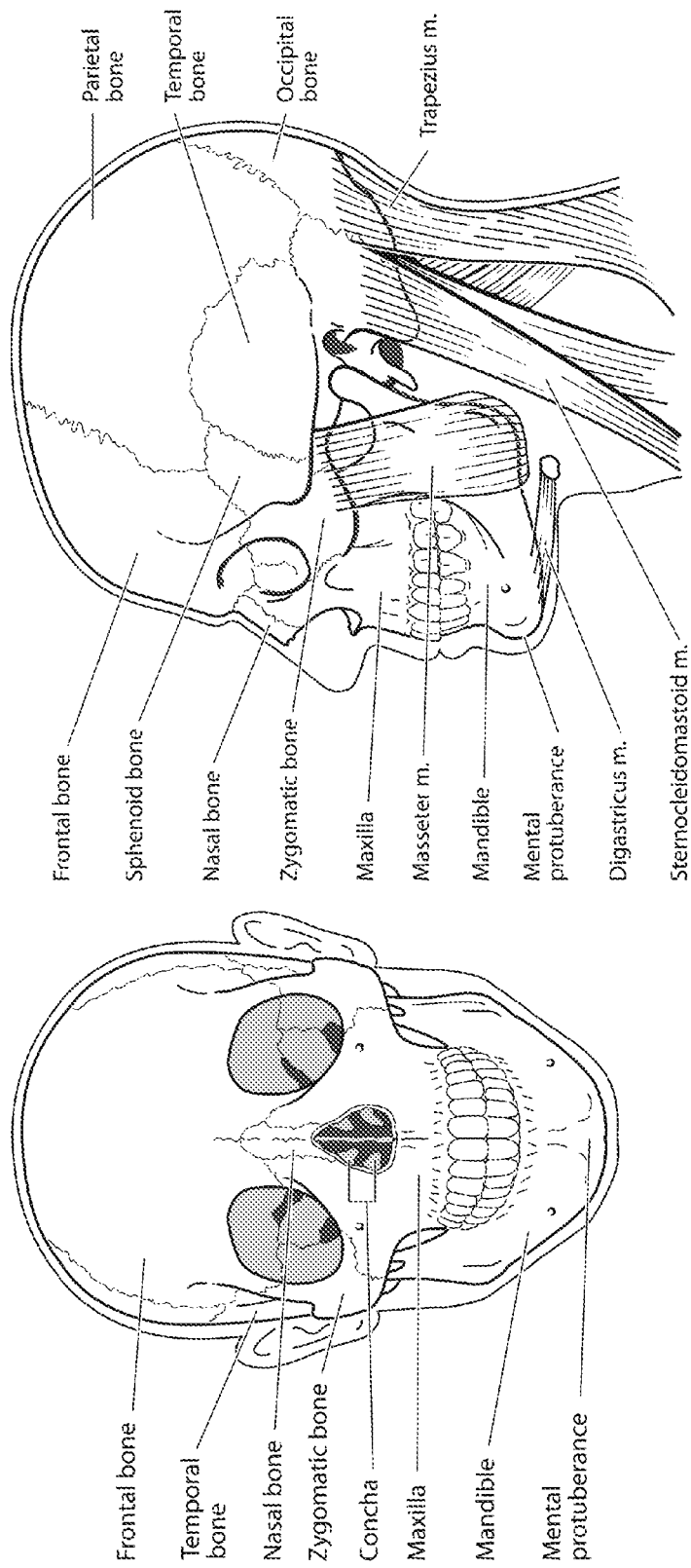

FIG. 2j shows a front view of the bones of a skull including the frontal, temporal, nasal and zygomatic bones. Nasal concha are indicated, as are the maxilla, mandible and mental protuberance.

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius.

Figure 3A:
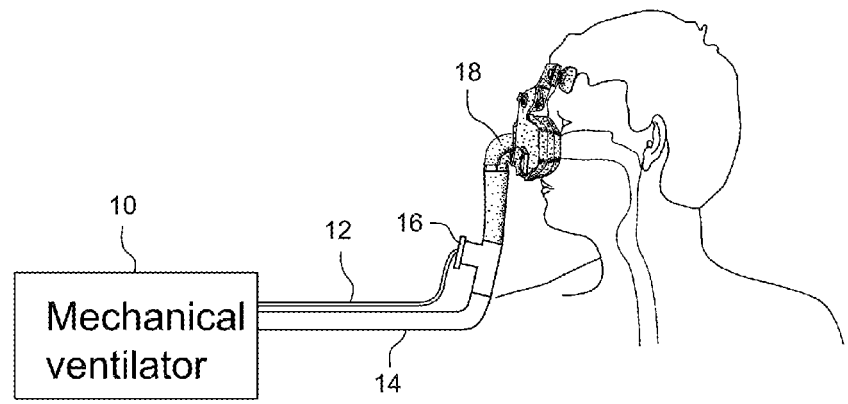

FIG. 3a is a diagram of a ventilation assembly in accordance with a related art.

Figure 3B:
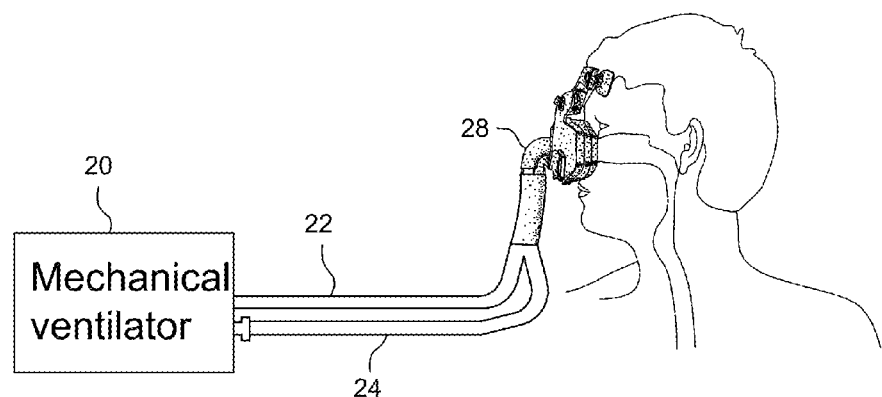

FIG. 3b is a diagram of another ventilation assembly in accordance with a related art.

Figure 4A:
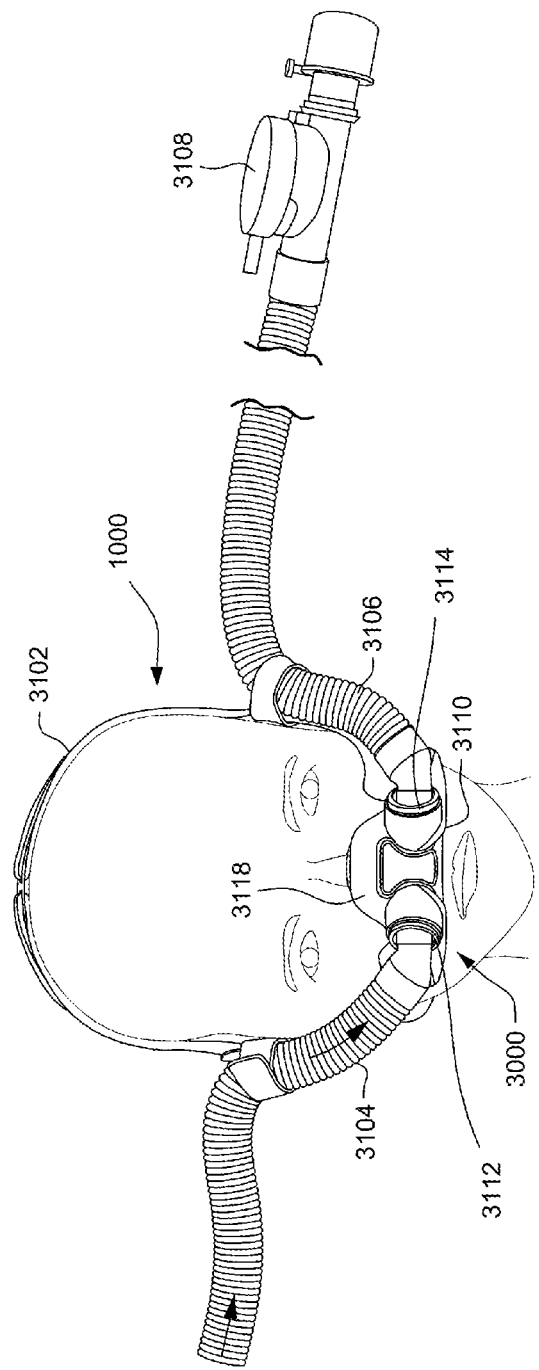

FIG. 4a is a front view of an exemplary mask assembly in accordance with the present technology depicting the inspiratory phase of ventilation.

Figure 4B:
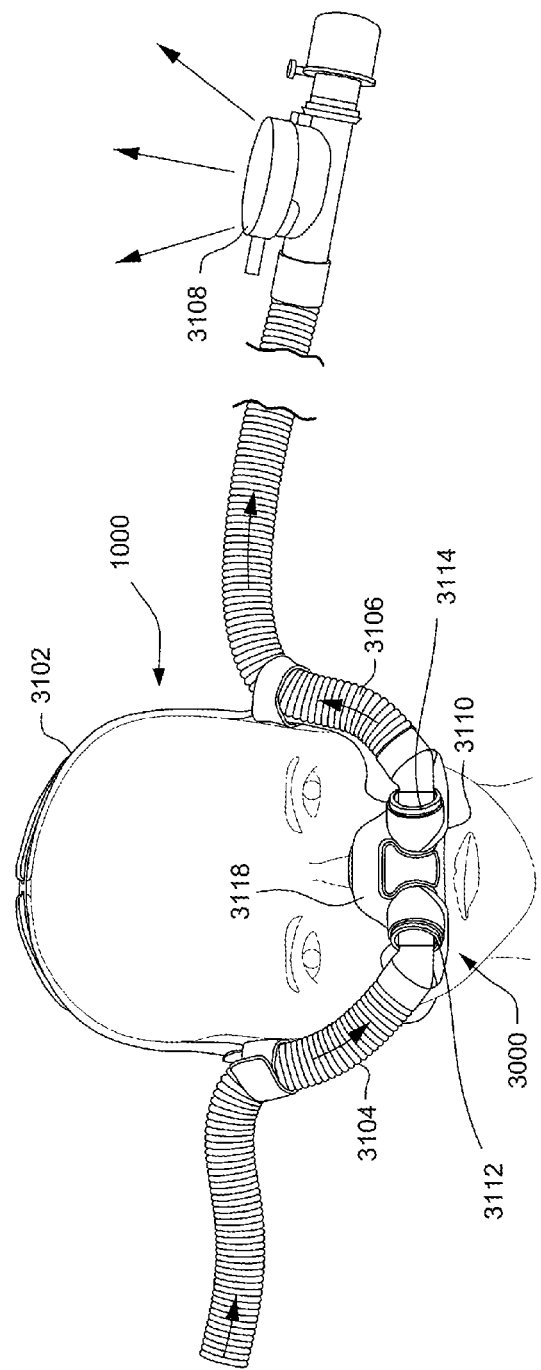

FIG. 4b is a front view of the exemplary mask assembly of FIG. 4a depicting the expiratory phase of ventilation.

Figure 5:
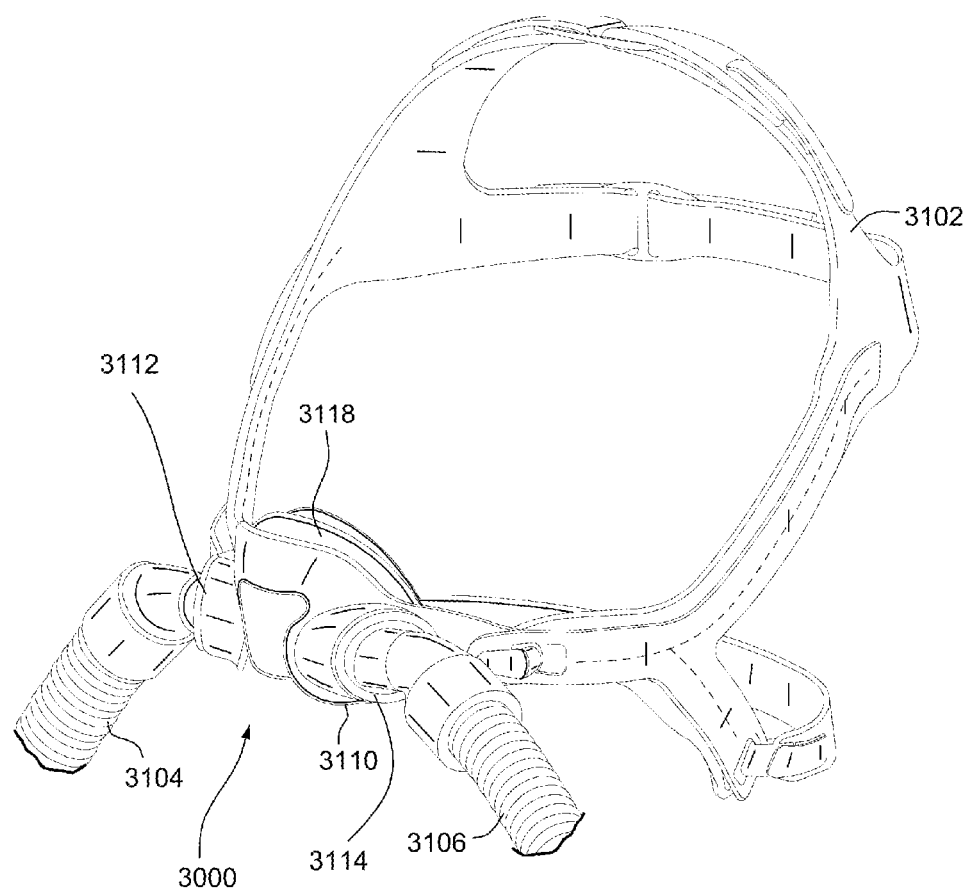

FIG. 5 is a perspective view of an exemplary mask assembly in accordance with the present technology, including headgear.

Figure 6A:
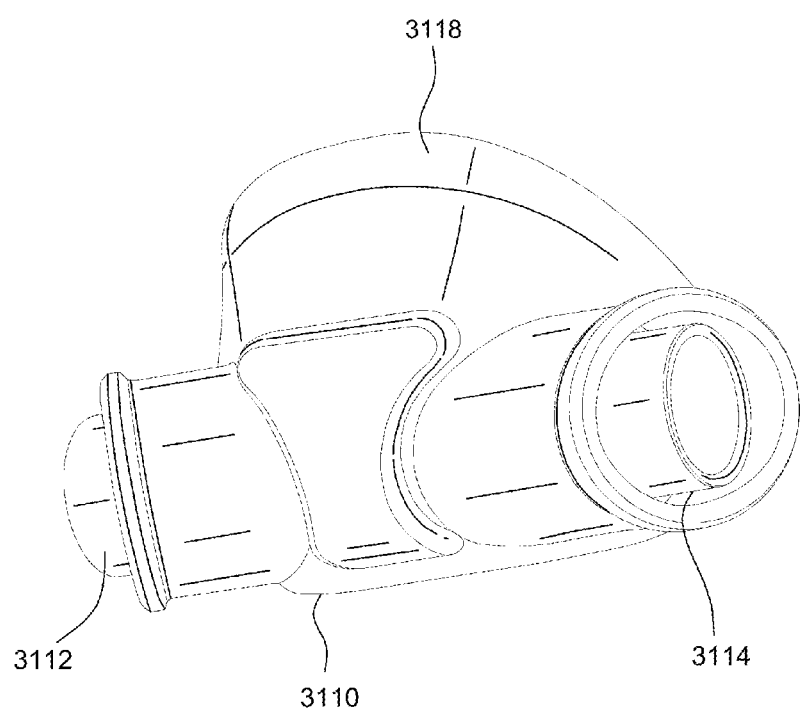

FIG. 6a is a front perspective view of an exemplary mask in accordance with the present technology.

Figure 6B:
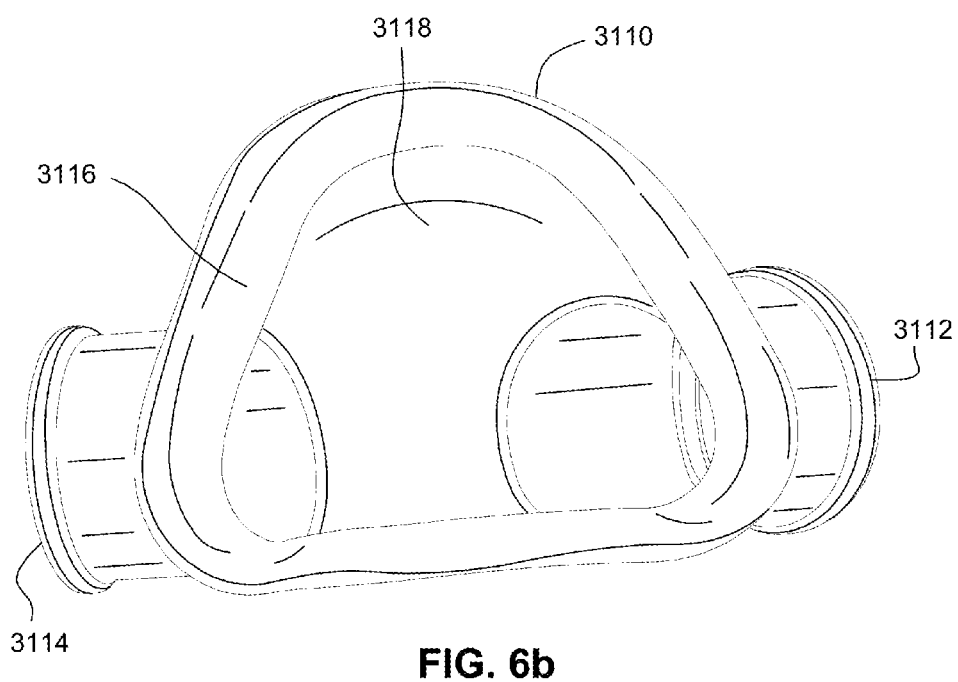

FIG. 6b is a rear perspective view of an exemplary mask in accordance with the present technology.

Figure 7:
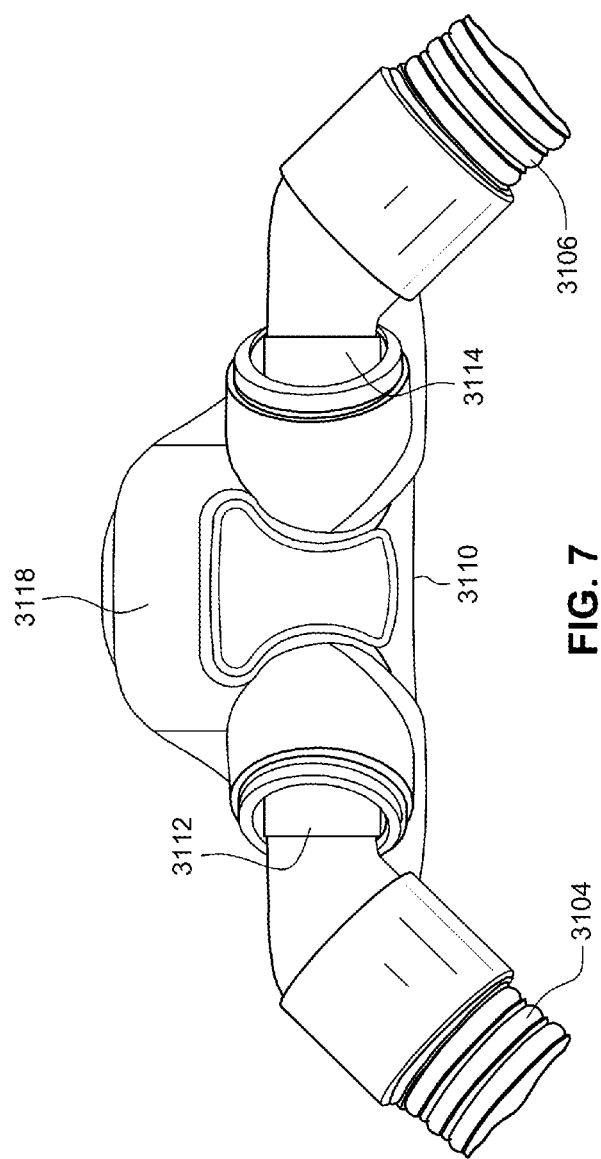

FIG. 7 is a front view of an exemplary mask assembly in accordance with the present technology.

Figure 8:
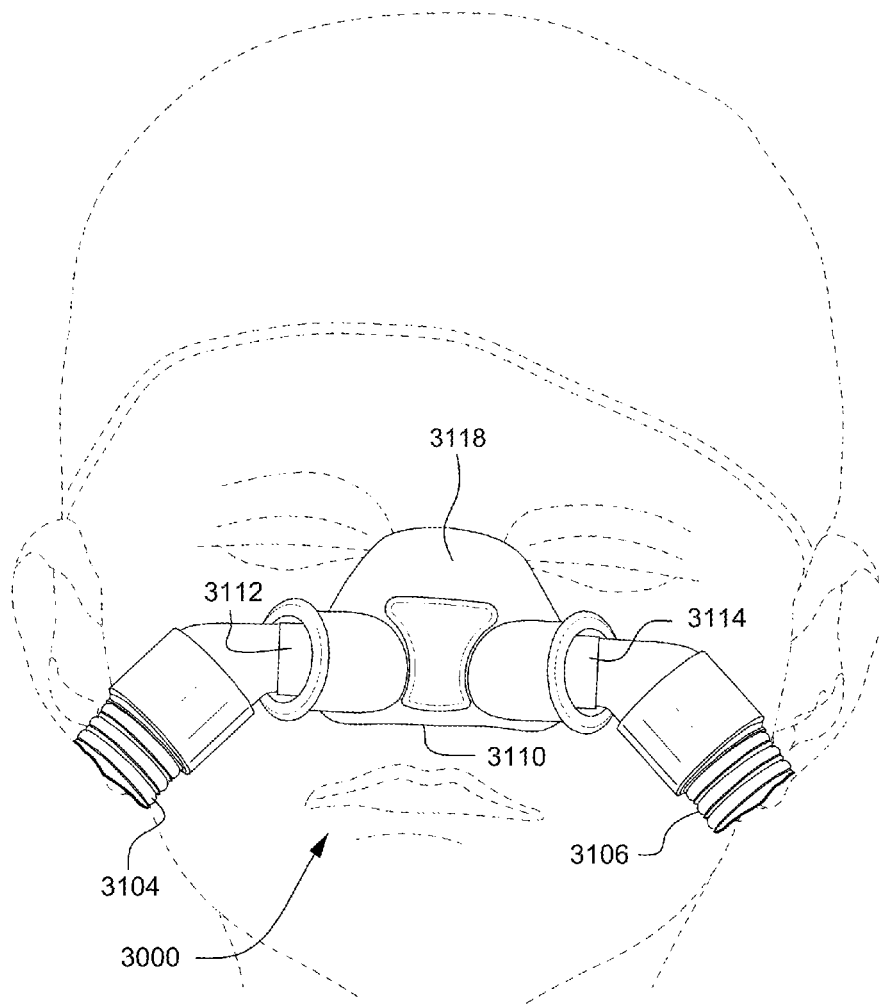

FIG. 8 is a front view of the exemplary mask assembly of FIG. 7, in an operational configuration.

Figure 9:
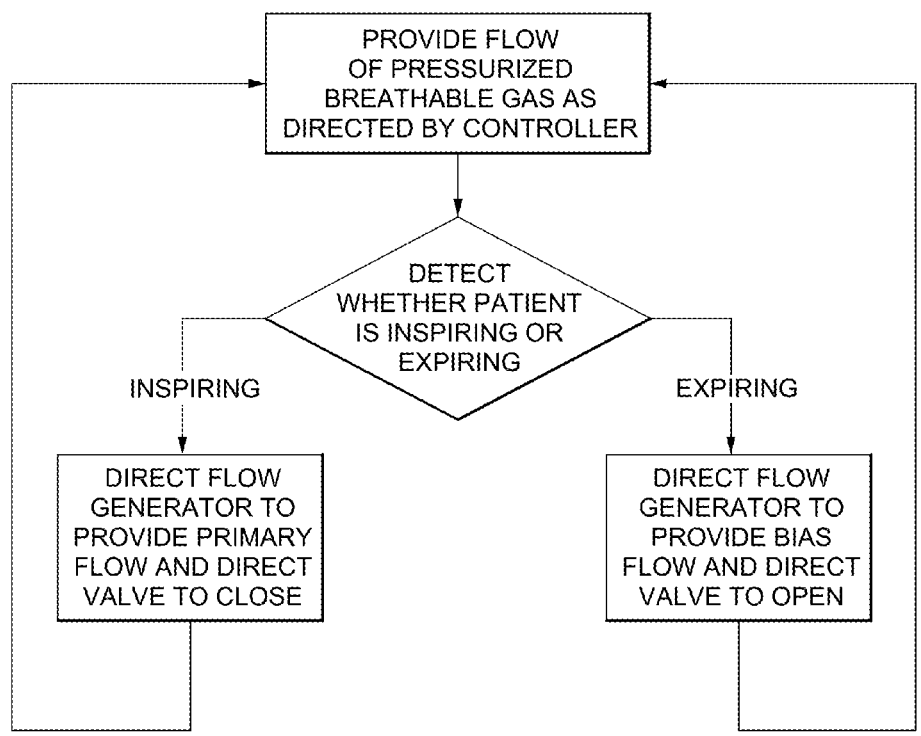

FIG. 9 is a flowchart of an exemplary method in accordance with the present technology.

Figure 10:
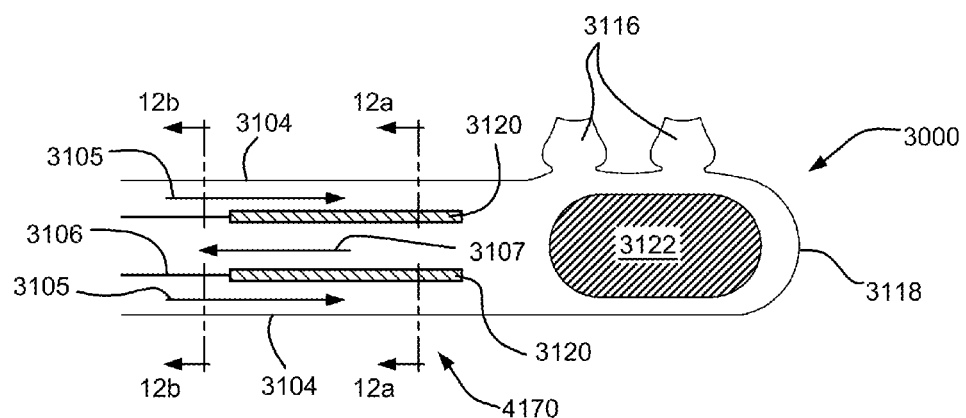

FIG. 10 shows a cross-sectional view of a conduit and a patient interface of a ventilation system according to an example of the present technology.

Figure 11:
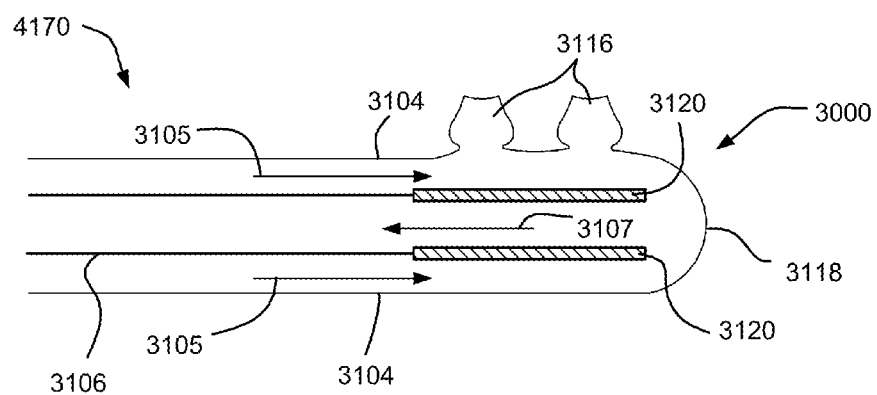

FIG. 11 shows a cross-sectional view of a conduit and a patient interface of a ventilation system according to another example of the present technology.

FIG. 12a shows a cross-sectional view of a conduit through line 12a-12a of FIG. 10 according to an example of the present technology.

FIG. 12b shows a cross-sectional view of a conduit through line 12b-12b of FIG. 10 according to an example of the present technology.

FIG. 12c shows a cross-sectional view of a conduit according to another example of the present technology.

FIG. 12d shows a cross-sectional view of a conduit according to another example of the present technology.

5 DETAILED DESCRIPTION OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Treatment Systems

Figure 1A:
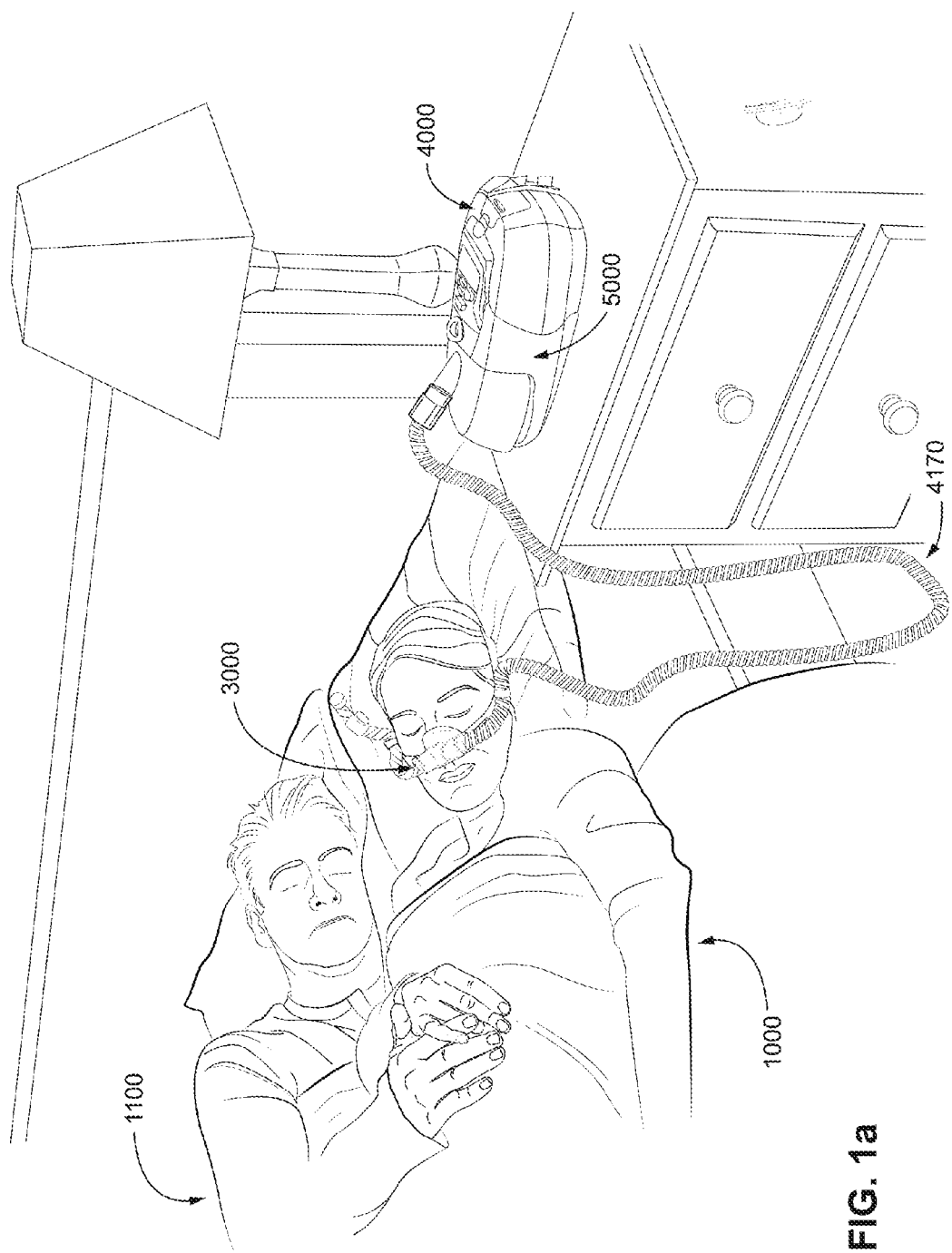

In one form, the present technology comprises an apparatus for treating a respiratory disorder. The apparatus, as can be seen in FIG. 1a, may comprise a flow generator or blower 4000 for supplying pressurised respiratory gas, such as air, to the patient 1000 via an air delivery tube 4170 leading to a patient interface 3000.

5.2 Therapy

In one form, the present technology comprises a method for treating a respiratory disorder comprising the step of applying positive pressure to the entrance of the airways of a patient 1000.

5.2.1 Related Art Therapy

When providing respiratory therapy to pediatric/infant patients via a non-vented mask, the dead space volume of the respiratory circuit can be critical in providing effective therapy, as well as preventing lung injury. Dead space volume of the breathing circuit represents the volume of air exhaled by the patient that is not removed from the system and will be re-inhaled at the next breath. Typically, exhaled air is removed by the force of exhalation and/or by a flow of gas generated by the respiratory therapy system. This volume does not contribute to gas exchange and adversely affects the applied therapy. Dead space volume of the breathing circuit is less of a concern for the adult population since the ratio of dead space volume to patient tidal volume is much smaller. However, the dead space volume is a much more substantial issue in pediatric respiratory medicine, as the respiratory circuit dead space volume in this case may be comparable to the tidal volume provided to the patient.

The need to remove the dead space volume can be explained in the following way. If a specific respiratory arrangement is associated with a large dead space volume, to achieve the same alveolar ventilation as compared to a system with no dead space, the breath rate and/or tidal volume have to be increased. An increase in the breath rate and tidal volume is associated with increasing the work of breathing and operating at a higher pulmonary pressure, respectively, which is not optimal. If the patient cannot tolerate an increase in breath rate and/or tidal volume, the patient may require sedation and/or intubation. Furthermore, ventilator-induced lung injury is directly related to the tidal volume provided. Since removing the dead space volume of the respiratory circuit may result in an equivalent reduction in tidal volume for a given amount of gas exchange, the reduction in dead space volume can minimize lung injuries.

Typically, clinicians use a custom-made mask of reduced size and improved fit, so as to minimize the dead space volume. This is a costly and incomplete solution which only partially reduces the dead space volume since the same air path is used for inspiration and expiration.

Alternatively, vented systems, based on permanently formed openings in the body of the mask, reduce and partially allow flushing of the dead space (depending on the position of the vent leak) from one breath to another. However, vented systems have certain disadvantages compared to non-vented systems. The expiratory resistance is higher which can lead to increased work of breathing. The positive end expiratory pressure (PEEP) cannot be set to zero and should be set high enough to avoid CO2 rebreathing, which can unnecessarily inconvenience the patient. When a vented system is used with oxygen, oxygen may be wasted through the permanently open vent.

FIG. 3a, which is a diagram of a ventilation system according to a related art, demonstrates the dead space volume problem. The system depicted is a single limb circuit and includes a mechanical ventilator 10, a supply conduit 14, a control line 12, an expiratory valve 16, and a non-vented mask 18.

Operation of the ventilation system may begin with the mechanical ventilator 10 supplying an inspiratory flow of gas through the supply conduit 14 to ventilate the patient during inspiration. Then, during expiration, the expiration valve 16 is opened, via control line 12, to allow exhalate to be directed away from the patient. Additionally, the mechanical ventilator 10 may provide a bias flow of less magnitude than the inspiratory flow along the supply conduit 14 to aid in flushing the exhalate. However, due to the location of the expiratory valve 16, a large amount of exhalate may remain in a portion of the breathing circuit because the bias flow cannot reach this portion of the air circuit, as the bias flow will instead exit via the expiratory valve 16. The portion upstream of the expiratory valve 16 that cannot be flushed by the bias flow represents the dead space volume and is indicated by stippling in FIG. 3a.

FIG. 3b is a diagram of a similar ventilation system, however, FIG. 3b shows a double limb circuit. The system includes a mechanical ventilator 20, a supply conduit 24, a non-vented mask 28 and a return conduit 22. The supply conduit 24, return conduit 22, and the non-vented mask 28 define a breathing circuit.

Operation of the ventilation system may be similar to the system shown in FIG. 3a. The mechanical ventilator 20 may supply the patient with an inspiratory flow via the supply conduit 24 during inspiration. Then, during expiration, the mechanical ventilator 20 may supply a bias flow that is of less magnitude than the inspiratory flow so as to flush exhalate from the breathing circuit. However, the bias flow may not be able to reach all sections of the mask and, therefore, to flush all of the exhalate from the breathing circuit. Thus, some exhalate remains upstream of the intersection of the supply conduit 24 and return conduit 22. This, again, represents the dead space volume and is represented by stippling in FIG. 3b.

5.2.2 Ventilation with Reduced Dead Space Volume

FIGS. 4a and 4b depict a system and method of ventilation in accordance with an example of the present technology. At the outset, while the examples depicted in FIGS. 4a-8 are designed for pediatric applications, it should be noted that the concepts, methods, systems, and apparatuses associated with the present technology may be equally applicable to all age groups.

FIG. 4a depicts the inspiratory phase of ventilation. During inspiration a flow generator 4000 may generate a flow of pressurized gas and apply it to an inlet limb 3104 at a distal end opposite of the proximal end connected to patient interface 3000. The patient interface 3000 in this view is shown donned on the patient and may be removably retained on the patient by a positioning and stabilising structure 3102 to be described in greater detail below. The inlet limb 3104 may be releasably connected to the patient interface 3000 at its proximal end. Specifically, the proximal end of inlet limb 3104 may be releasably connected to mask 3110 to partly define a breathing circuit. An outlet limb 3106 may be releasably connected at the side of the mask 3110 opposite to the side of the connection to the inlet limb 3104, which may also partly define the breathing circuit. At the end of the outlet limb 3106 opposite the end connected to the mask 3110, a controllable valve 3108 may be attached. A breathing circuit may therefore be defined from the flow generator 4000, through the inlet limb 3104, into the mask 3110 and the plenum chamber 3118 defined thereby, through the outlet limb 3106, and to the controllable valve 3108. Alternatively, a controllable opening or an actuator may be used in place of the controllable valve.

During inspiration, the flow generator 4000 may generate a flow of pressurized gas through the inlet limb 3104 to the mask 3110 to insufflate the patient. Also during inspiration, the outlet limb 3106 may be closed from atmosphere. For example, the controllable valve 3108 may used and may be in a closed configuration to substantially seal the flow of pressurized gas in the breathing circuit from atmosphere. Since the breathing circuit will be substantially sealed by closure of the controllable valve 3108, the pressurized gas may be directed into the respiratory system of the patient. In FIG. 4a the arrows indicate the inspiratory flow path by which gas flows. It should be noted that the flow of gas is not indicated as extending along the breathing circuit beyond the mask 3110, however it should also be understood that some flow of gas may travel into the outlet limb 3106.

During expiration, the flow generator 4000 may not generate a flow of pressurized gas at all or the flow generator 4000 may generate a bias flow of pressurized gas. The bias flow may be lesser in magnitude than the primary inspiratory flow. Also, during expiration, the outlet limb may be opened to atmosphere. For example, the controllable valve 3108 may be used and may be placed into an open configuration to allow the expulsion of gas from the breathing circuit to atmosphere. By opening the controllable valve 3108, exhalate (e.g., $CO_2$) may be substantially purged from the breathing circuit to prevent rebreathing by the patient. In FIG. 4b the arrows also indicate the path by which gas flows. The arrows on the inlet limb 3104 may indicate the bias flow and the arrows on the outlet limb 3106 may indicate the expiratory flow path of exhalate toward the controllable valve 3108. The arrows emanating from the controllable valve 3108 may indicate the flow of gas, including exhalate, to atmosphere. The bias flow provided during expiration may prevent exhalate in the breathing circuit from flowing upstream. For example, the bias flow may prevent exhalate from flowing upstream into the inlet limb 3104 from the mask 3110. Also, the bias flow may prevent exhalate in the outlet limb 3106 that was not exhausted during a previous expiration phase, from flowing upstream into the mask 3110.

Additionally, at least one sensor (not shown) may be provided to the ventilation system to detect whether the patient is inspiring or expiring. In such a situation the at least one sensor may be able to detect inspiration of the patient and generate a signal that is indicative of inspiration. In response to this signal the controllable valve 3108 may be placed into the closed configuration and the flow generator 4000 may provide a primary flow of pressurized gas to the patient through the inlet limb 3104 to the mask 3110. The at least one sensor may also be able to detect expiration of the patient and generate a signal that is indicative of expiration. In response to this signal the controllable valve 3108 may be placed into the open configuration and the flow generator 4000 may provide no flow of pressurized gas or a bias flow of pressurized gas to the patient through the inlet limb 3104 to the mask 3110.

Based upon the arrangement of the inlet limb 3104 and the outlet limb 3106 on the mask 3110, a substantially unidirectional and/or linear path may be defined for the flow of gas. By locating the inlet limb 3104 and the outlet limb 3106 substantially coaxially disposed on opposite sides of the plenum chamber 3118 formed by the mask 3110, it may be possible to provide a direct flow path away from the plenum chamber. This arrangement may be advantageous to minimize the dead space volume. In addition the defined cross flow flushes very efficiently any remaining dead space to wash out any exhaled $CO_2$. By providing a bias flow from the flow generator 4000 to the mask 3110 through the inlet limb 3104 the plenum chamber 3118 defined by mask 3110 may substantially flushed or purged of exhalate during expiration. In other words, in the described arrangement the path by which pressurized gas may be provided to the patient along inlet limb 3104, is to a large extent, separated from the path by which exhalate is discharged from the plenum chamber 3118, defined by the mask 3110 through the outlet limb 3106. By separating these paths, the region of the breathing circuit common to the inspiratory flow path and the expiratory flow path, as shown in FIGS. 3a and 3b, may be eliminated which, in turn, may reduce the dead space volume because the space in which exhalate may linger is reduced.

It should also be understood that at least two factors are of significance with regard to the length of the outlet limb 3106. The longer outlet limb 3106 is the greater the expiratory resistance. Thus, the outlet limb 3106 should be sufficiently short so as not to provide excessive resistance to the patient's expiration. However, the controllable valve 3108 may be noisy during operation. Therefore, the outlet limb 3106 must be sufficiently long to distance the controllable valve 3108 from the patient so as not to be disruptive.

As to the controllable valve 3108, this valve may be variable between open and closed configurations. In other words, it may include a position wherein the controllable valve 3108 is completely open, allowing the maximum outflow of gas, and it may also include a position wherein the controllable valve 3108 is completely closed, to prevent any outflow of gas. In addition to the completely open and completely closed positions, the controllable valve 3108 may also he variable therebetween such that the controllable valve 3108 may allow some outflow of gas that is lesser in magnitude than when the controllable valve 3108 is in the completely open position. During inspiration, the controllable valve 3108 may be kept slightly open to promote $CO_2$ wash out and prevent back flow of $CO_2$. This function of the controllable valve 3108 may be achieved by an aperture or opening having a variable aperture or opening size, such that in a first configuration the aperture is open and in at least one additional configuration that is different from the first configuration the aperture may be closed.

Additionally, in certain examples of the technology the system may include a controller that may control the flow generator 4000 and the controllable valve 3108. The controller may also be in communication with the at least one sensor which may detect whether the patient is inspiring or expiring such that it may coordinate the function of the flow generator 4000 and the controllable valve 3108. Also, in such examples of the technology the controller may control the controllable valve 3108 by pneumatic actuation (e.g., through a tube) and/or by electrical actuation (e.g., through a wire). The tube or wire may connect to the controllable valve 3108 by being placed along the conduit 4170, either inside or outside, and following along the inlet limb 3104, across the mask 3110, and along the outlet limb 3106. Alternatively, the tube or wire may be separate from the conduit 4170 and not follow the path of the inlet limb 3104 and the outlet limb 3106 to the controllable valve 3108.

A controller may include a central processing unit or CPU, a system bus that communicates with RAM and storage or a memory device. The storage can be magnetic, flash based, solid state, or other storage technology. The system bus may also communicate with a user input adapter that allows users to input commands to the processing system via a user input component (e.g., a touch input element or the like) and/or buttons. The memory device may be included to store the functional parameters inputted to the controller.

FIG. 9 depicts a method of ventilating a patient according to an example of the present technology. In this exemplary method, the flow generator 4000 may provide a flow of pressurized breathable gas to the patient through the inlet limb 3104. At least one sensor may detect whether the patient is inspiring or expiring. The sensor may then generate a signal indicative of inspiration or expiration. Based on this signal the controller may direct the controllable valve 3108 to move to the open configuration when expiration is detected to allow the discharge of exhalate, or the controller may direct the controllable valve 3108 to move to the closed configuration to prevent the escape of pressurized breathable gas intended to insufflate the patient during inspiration. Also, the controller, based on the signal from the at least one sensor, may instruct the flow generator 4000 whether to provide a primary flow or a bias flow. When a signal indicative of inspiration is generated by the at least one sensor, the controller may instruct the flow generator 4000 to provide a primary flow of pressurized breathable gas to insufflate the patient. Alternatively, when a signal indicative of expiration is generated by the at least one sensor, the controller may instruct the flow generator 4000 to provide a bias flow to, at least partially, flush the breathing circuit of exhalate.

5.3 Patient Interface

A non-invasive patient interface 3000 in accordance with one aspect of the present technology, as shown in FIGS. 4a, 4b, 5, 6a, and 6b, comprises the following functional aspects; a seal-forming structure 3116 (shown in FIG. 6b), a plenum chamber 3118 (shown in FIG. 6b) defined by the mask 3110, a positioning and stabilising structure 3102 and connection ports 3112, 3114 for connection to an air circuit having an inlet limb 3104 and an outlet limb 3106. In some forms a functional aspect may be provided by one or more physical components. In some forms, one physical component may provide one or more functional aspects. In use, the seal-forming structure 3116 is arranged to surround an entrance to the airways of the patient so as to facilitate the supply of air at positive pressure to the airways. A related patient interface is disclosed in U.S. patent application Ser. No. 13/097,501, the entire contents of which are hereby incorporated by reference.

The term "patient interface", for the purposes of the present disclosure, is intended to refer to various interface types such as a full face mask, a nasal mask, an oro-nasal mask, nasal puffs or pillows, an oro-nasal mask, and an endotracheal tube. In other words, any device that facilitates an interface with an entrance to the patient's airways for the supply of pressurized breathable gas may be a "patient interface". It should also be understood that those skilled in the art would also understood the term "mask" to refer broadly to the various forms of patient interface described above. Thus, for example, a mask may include a full face mask, a nasal mask, an oro-nasal mask, nasal puffs or pillows, an oro-nasal mask, or an endotracheal tube.

5.3.1 Patient Interface (Mask)

The mask 3110 is depicted in use on a patient in accordance with an example of the present technology in FIGS. 4*a* and 4*b*. Positioning and stabilising structure 3102 (e.g. headgear) may be attached to the mask 3110 to retain the mask on the patient's head during therapy. The mask 3110 may be connected to an inlet limb 3104 and an outlet limb 3106 to provide inspiratory and expiratory flows through a breathing circuit defined by these components. Also, the mask 3110 may be a non-vented mask according to one example of the present technology. The mask 3110 may also be a nasal mask or a full-face mask.

in FIG. 5, an exemplary mask 3110 is shown in perspective connected to the positioning and stabilising structure 3102 (e.g., headgear). The mask 3110 is also shown connected to an inlet limb 3104 and outlet limb 3106. Again, the mask 3110 may be non-vented in accordance with an example of the present technology.

In FIGS. 6*a* and 6*b*, only the mask 3110 is shown in front and rear perspective views. FIG. 6*a* shows the mask 3110 in a front-perspective view. The mask 3110 shown in this view is non-vented in accordance with an example of the present technology. Also, the mask 3110 includes an inspiratory port 3112 and an expiratory port 3114 on opposite sides of the mask in a cross-flow configuration. The inspiratory port 3112 may be connected to an inlet limb 3104, as shown in other views, and the expiratory port 3114 may be connected to an outlet limb 3106, as shown in other views. As can be seen in this exemplary view, the inspiratory port 3112 and the expiratory port 3114 may be located on the mask 3110 in a substantially coaxial manner. The inspiratory port 3112 and the expiratory port 3114 may also be located on the mask 3110 such that a substantially pneumatically unobstructed path from the inspiratory port through the mask to the expiratory port is defined therethrough. In other words, the inspiratory port 3112 and the expiratory port 3114 may be located on the mask 3110 such that during therapy pressurized gas may be able to flow unidirectionally and/or linearly therethrough. During therapy this may allow an exemplary ventilation system incorporating such a mask 3110 to provide pressurized gas to the patient such that there is substantially no backflow through the inspiratory port 3112.

As the plenum chamber 3118 in the illustrated example is also located along the flow path between the coaxially disposed inspiratory port 3112 and the expiratory port 3114, the ventilation flow can pass across the plenum chamber 3118, thus substantially reducing (and effectively eliminating) any dead space. This is even more so when the plenum chamber 3118 is coaxially disposed somewhere between the inspiratory port 3112 and the expiratory port 3114. The fact that the inspiratory port 3112, the plenum chamber 3118 and the expiratory port 3114 in this case are located on a straight line ensures that, during therapy, the pressurized gas is able to flow unidirectionally and substantially linearly therethrough, thus optimising the ventilation flow and ensuring an even more effective evacuation of the chamber.

FIG. 6*b* shows a rear perspective view of a mask 3110 according to an example of the present technology. This view also shows the inspiratory port 3112 and the expiratory port 3114 located on opposite sides of the mask 3110 in a cross-flow configuration. This view also shows the mask 3110 having a seal-forming structure 3116 to contact the skin of the patient. The seal-forming structure 3116 also aids the mask 3110 in defining, at least in part, a gas chamber along with a portion of the face of the patient. The seal-forming structure 3116 will be discussed in greater detail below. In this view it is also possible to see an interior portion of the mask 3110 that, in conjunction with the seal-forming structure 3116, may partially define the gas chamber when the mask is donned by the patient.

FIG. 7 shows a front view of the mask 3110 according to an example of the present technology with an inlet limb 3104 connected to the mask at the inspiratory port 3112 and an outlet limb 3106 connected to the mask at the expiratory port 3114. Also in this view, it can be seen that the inspiratory port 3112 and the expiratory port 3114 are located on opposite sides of the mask 3110. Such an arrangement may allow the flow of pressurized gas to pass through the mask substantially unidirectionally and/or linearly such that there is no backflow through the inspiratory port.

FIG. 8 shows a similar view to FIG. 7 with the mask 3110 donned on a patient shown in dashed lines. In this particular example the mask 3110 is a nasal mask. Also in this view, it can be seen that the inlet limb 3104 and the outlet limb 3106 extend away from the mask in opposite directions at opposite sides of the patient.

5.3.2 Seal-Forming Structure

In one form of the present technology, a seal-forming structure 3116 provides a sealing-forming surface, and may additionally provide a cushioning function.

Preferably a seal-forming structure 3116 in accordance with the present technology is constructed from a soft, flexible, resilient material such as silicone.

In one form the non-invasive patient interface 3000 comprises a seal-forming portion that forms a seal in use on an upper lip region (that is, the lip superior) of the patient's face.

5.3.3 Plenum Chamber

Preferably the plenum chamber 3118 defined by the mask 3110 has a perimeter that follows the shape of the seal-forming structure 3116, as can be seen in FIG. 6*b*, and is shaped to be complementary to the surface contour of the face of an average person in the region where a seal will form in use. Actual contact with the face is provided by the seal-forming structure 3116. Preferably the seal-forming structure 3116 extends in use about the entire perimeter of the plenum chamber 3118 defined by the mask 3110.

5.3.4 Positioning and Stabilising Structure

Preferably the seal-forming structure 3116 of the patient interface 3000 of the present technology is held in sealing position in use by the positioning and stabilising structure 3102. As shown in FIG. 5, the positioning and stabilising structure 3102 may comprise a plurality of straps. Also, the positioning and stabilising structure 3102 may be a headgear. The positioning and stabilising structure 3102 may also be removably or fixedly connected to the mask 3110.

5.3.5 Ports

In one form of the present technology, as in FIGS. 6a and 6b, a patient interface 3000 includes one or more ports, that allow access to the volume within the plenum chamber 3118 defined by the mask 3110. In one form this allows a clinician to supply supplemental oxygen. In one form this allows for the direct measurement of a property gases within the plenum chamber 3118 defined by the mask 3110, such as the pressure.

FIGS. 6a and 6b, in particular, depict an inspiratory port 3112 and an expiratory port 3114 disposed on opposite sides of a mask 3110. The inspiratory port 3112 and the expiratory port 3114 are adapted to connect to conduits such as an inlet limb 3104 and an outlet limb 3106. In the examples shown in these view the inspiratory port 3112 and the expiratory port 3114 may have a substantially circular cross-section. The inspiratory port 3112 and the expiratory port 3114 may also include features to allow removable attachment of the inlet limb 3104 and outlet limb 3106. The inspiratory port 3112 and the expiratory port 3114 may also provide a sealed pneumatic path between respective inlet and outlet limbs 3104, 3106 and the plenum chamber 3118 defined by the mask 3110.

5.4 Exchanger

When providing therapy to a patient, e.g., by ventilation as described above, it may be advantageous to provide a humidified and/or heated flow of gas to the patient's airways to prevent undesirable effects such as drying of the airways. In one example, a humidifier may be provided upstream of the patient's airways to heat and/or humidify the flow of gas to the patient's airways. In further examples, as will be discussed in greater detail below, it may be advantageous to transfer heat and/or moisture between the patient's exhalate prior to discharging the exhaled gas to atmosphere and the flow of gas before it reaches the patient's airways. An exchanger 3120 may be provided to the patient interface 3000, e.g., in the mask 3110, to transfer heat and/or moisture between the patient's exhalate and the flow of gas before it reaches the patient's airways. Examples of exchangers are disclosed in International Application No. PCT/AU2012/001382, which is incorporated herein by reference in its entirety.

As illustrated in FIGS. 10 and 11, some examples of the present technology may implement an exchanger 3120, such as in a conduit 4170 for air or other breathable gas that is directed to a respiratory system of a patient. FIGS. 10 and 11 shows cross-sectional views of examples of a conduit 4170 and a patient interface 3000 taken longitudinally. The exchanger 3120 may be coupled to or integrated with a patient interface 3000, such as a respiratory nasal mask, nose and mouth mask, full face mask, endotracheal tube, cannula, nasal prongs, nasal pillows, etc. The exchanger 3120 may be a component of a conduit assembly 4170 such as an inlet limb 3104 and an outlet limb 3106. The conduit 4170 may be coupled with an output of a flow generator 4000, such as a respiratory treatment apparatus, so that the conduit 4170 may direct respiratory treatment to the patient. The exchanger 3120 may condition the inspiratory flow with the expiratory flow or vice versa and may do so without powered heating coils. The exchanger 3120 may separate, or form at least a portion of a barrier that divides or separates, an inspiratory flow path 3105 and an expiratory flow path 3107 of the conduit 4170. In this regard, these flow paths 3105, 3107 can provide a unidirectional flow characteristic such that each flow path may be implemented to generally only conduct breathable gas in one direction. In this regard, in the case of the inspiratory flow path 3105, an inspiratory flow will be directed toward a patient interface 3000 such that the inspiratory flow may be inspired by a user of the patient interface 3000. Similarly, in the case of the expiratory flow path 3107 an expiratory flow will be directed away from the patient interface 3000 such that the expiratory flow will have been expired by a user of the patient interface 3000.

In some examples, the unidirectional flow of the flow paths 3105, 3107 may be maintained by optional valves. For example, at least one one-way valve may control the flow through the flow paths. An inspiratory' one-way valve may permit air flow in the direction from atmosphere to enter the inspiratory flow path 3105 but would impede or prevent a reverse of such air flow in the inspiratory flow path. Thus, the inspiratory valve would be open during patient inspiration and closed during patient expiration. Similarly, an expiratory one-way valve may permit air flow in the direction to atmosphere (away from patient interface 3000) so as to exit the expiratory flow path 3107 but would impede or prevent a reverse of the illustrated flow through the expiratory channel. Thus, the expiratory valve would be open during patient expiration and closed during patient inspiration.

As a result of the configuration of the flow paths 3105, 3107 and the exchanger 3120, the exchanger 3120 may be exposed to inspiratory flow and expiratory flow but on opposing sides of the exchanger 3120. In this sense, it may generally have an inspiratory side that is not generally exposed to expired air but only fresh inspired air or gas and an expiratory side that is not generally exposed to fresh air before inspiration but only expired air. Thus, the exchanger 3120 may conduct or transfer a component of either the expiratory gas or inspiratory gas to the other in association with these sides. For example, the exchanger 3120 may be configured to conduct heat to serve as a heat exchanger. In such a case, warm expired air of the expiratory flow path 3107, which may be warmed by the patient, may contact the exchanger 3120 on an expiratory side. Thus, the expiratory air may warm the exchanger 3120. The exchanger 3120, which may be formed or extruded of a heat conductive material such as silver, copper, gold, aluminum or a dust or composite of any of those materials etc., may conduct that heat energy to the inspiratory side of the exchanger 3120. The inspiratory flow of the inspiratory flow path 3120 may then contact the inspiratory side and absorb the warmth that may be conducted, convected or radiated by the exchanger 3120 if the inspiratory flow is cooler than the exchanger 3120. In the case of a warm environment, the temperature of the exchanger 3120 may even potentially cool an inspiratory flow that is warmer than the expiratory flow.

Thus, the patient's own respiration may be applied to condition the temperature (e.g., heat or cool) of the inspired air through the exchanger 3120. Moreover, since the inspiratory flow path 3105 and expiratory flow path 3107 may be divided by the exchanger 3120, the exchange of temperature may take place in a manner that minimizes potential for rebreathing of expired carbon dioxide. In this regard, the distinct inspiratory and expiratory flow paths 3105, 3107 may permit the exchange without substantially increasing dead space 3122. Dead space 3122 may be considered, as described above, the gas/space in the conducting areas of a respiratory system. In devices, such as the conduits of a respiratory treatment apparatus, it may refer to the same volume/space through which a patient is breathing. In a single pathway device where both inspiratory and expiratory gas flows to/from the patient, the patient may re-breathe some of the air previously breathed out. Having a dual/separate inspiration and expiration pathways, the patient is substantially consistently breathing in 'fresh' air from the inspiration pathway while breathing out to the distinct expiration pathway.

The exchanger 3120, serving as a heat exchanger, may also reduce the output requirements or need for some heating components that are typically employed to warm fresh inspired air. For example, the use of the exchanger 3120 may reduce the size needed for heating coils or the energy used by such heating coils to heat inspired air to a comfortable temperature.

Similarly, in some examples, the exchanger 3120 may be implemented to transfer a moisture component of either the expiratory gas or inspiratory gas to the other. For example, expiratory flow may typically include a degree of moisture that may be greater than atmospheric air. The moisture of the expiratory flow may be absorbed by a material of the exchanger 3120, such as a hydrophilic material, a capillary material, a cellulose membrane, or a hydrogel, a polysulfone ether, a bio-compatible polymer, etc. The moisture may condense on a surface of a material of the exchanger on the expiratory side of the exchanger 3120. The moisture may then transfer through the exchanger 3120 to the inspiratory side. Inspiratory flow across the surface of the inspiratory side of the exchanger 3120 may then permit the moisture to evaporate into the inspiratory flow of the inspiratory flow path 3105. In some examples, the exchanger 3120 may be formed by a hydrophilic material or coating on one side and a hydrophobic material or coating on the other such as to promote the absorption of liquid in one channel and the evaporation of liquid in the other. For example, the inspiratory side of the exchanger 3120 may have a hydrophobic material or coating and the expiratory side of the exchanger 3120 may have a hydrophilic material or coating. Thus, the exchanger may be used to transfer heat and/or humidity from the breathable air in the expiratory path to the breathable air in the inspiratory path.

In contrast, in the case of a warm and humid environment surrounding the patient, if a warm and humid air is provided in the inspiratory path that is warmer than the expiratory flow, the exchanger 3120 may potentially cool and/or reduce the humidity of the inspiratory flow. In any case that liquid is transferred from one flow channel to another flow channel, the exchanger 3120 may take advantage of evaporative cooling, as the liquid is vaporized by the flow in either flow path, to cool the respective flow. For example, in the case where moisture is condensed in the expiratory flow path 3107 and transferred to the inspiratory flow path 3105 in liquid form, the liquid is vaporized by the flow in the inspiratory flow path 3105, which may result in cooling of the inspiratory gas.

Thus, the exchanger 3120, serving as a humidity exchanger, may be implemented to condition the humidity of the inspiratory flow from the humidity of the expiratory flow. Moreover, since the inspiratory flow path 3105 and expiratory flow path 3107 are divided by the exchanger 3120, the exchange of humidity may take place in a manner that minimizes potential for rebreathing of expired carbon dioxide or without substantially increasing dead space 3122 as previously mentioned. The exchanger 3120, serving as a moisture exchanger, may also reduce the output requirements or need for some humidification components that are typically employed to humidify inspired air. For example, the use of the exchanger 3120 may reduce the quantity of reservoir water needed for a humidifier. Similarly, it may also reduce the energy used by heating coils that heat water to humidify inspired air.

In some examples, one or more materials of the exchanger 3120 may be treated or chosen for particular performance characteristics. For example, as previously mentioned, the exchanger 3120 may include coatings of hydrophobic and/or hydrophilic materials. In some examples, a material of the exchanger 3120 may be coated to reduce carbon dioxide transfer or diffusion through the material. For example, an anti-carbonation coating may be applied to an exchanger material such as a cellulose membrane or a poly-sulfone-ether material. Such a barrier coating may still permit a transfer of water while impeding a transfer of carbon dioxide.

In some examples (not shown in the figures), the efficiency of the exchanger 3120 may be controlled, e.g., manually or automatically, to satisfy a patient's preferences. For example, in some examples the exchanger 3120 may be adjustable to permit greater and lesser surface area of the exchanger 3120 to be contacted by inspiratory and/or expiratory flow. In such as case, greater surface area may permit more humidity or heat transfer and less surface area may permit less humidity or heat transfer. For example, in examples utilizing fins, an adjustment mechanism, such as a rotary control, slider, motor or solenoid, may withdraw or extend less or more of the area of fins into the flow paths 3105, 3107 of the conduit 4170. Similarly, an adjustable cover(s) may extend or retract to different degrees to provide a movable barrier or insulator on one or more portions of the exchanger 3120 to change the contact area of the exchanger 3120 that can contact the flow in one or more flow paths 3105, 3107 of the conduit to impede the exchanger's 3120 efficiency to varying degrees. In some cases, automated control of the adjustment mechanism may involve evaluation, such as by a processor-based controller, of signals from one or more sensors, such as a humidity and/or temperature sensor that may be located proximate to either flow path 3105, 3107 of the conduit 4170, in the setting of the portion or size of the area of the exchanger 3120 that can participate in the exchange transfer. The controller or processor, which may also be a controller of a flow generator 4000, may be configured and adapted to implement the control methodologies. Thus, the controller may include integrated chips, a memory and/or processor control instructions or data in an information storage medium. For example, programmed instructions encompassing the control methodology may be coded on integrated chips in the circuits or memory of the device or such instructions may be loaded as software or firmware using an appropriate medium containing the instructions or data.

FIG. 10 shows an example of a patient interface 3000 with the exchanger 3120 positioned in the conduit 4170 to facilitate heat and/or moisture exchange between the inspiratory flow path 3105 and the expiratory flow path 3107. The inlet limb 3104 and the outlet limb 3106 may be arranged coaxially to reduce the dead space 3122. However, to accomplish heat and/or moisture transfer from exhalate to inhalate via an exchanger using a patient interface 3000 as depicted, for example, in FIGS. 4a and 4b, it would be necessary to bend back the outlet limb 3106 to be positioned near the inlet limb 3104 such that the exchanger 3120 could communicate with both limbs while maintaining the cross-flow arrangement. This may be undesirable for the patient as this arrangement may be bulky and/or unsightly. Thus, using the coaxial arrangement depicted in FIG. 10, for example, may allow for a similar flow pattern to minimize dead space while allowing the exchanger to communicate with the inlet limb 3104 and the outlet limb 3106.

In the example shown in FIG. 10, the conduit 4170 includes the inlet limb 3104 positioned externally around the outlet limb 3106. Thus, the inspiratory flow path 3105 may direct a flow of pressurized, breathable gas to the patient interface 3000, into the plenum chamber 3118 and through the seal-forming structure 3116 to the patient's airways. An exchanger 3120 can be seen positioned between the inspiratory flow path 3105 and the expiratory flow path 3107. When the patient exhales gas, the exchanger 3120 may recover heat and/or moisture from the patient's exhalate and transfer the heat and/or moisture to the flow of pressurized, breathable gas provided to the patient's airways along the inspiratory flow path 3105. The exhalate may then be discharged to atmosphere via the expiratory flow path 3107.

The example depicted in FIG. 10 also shows that there may be an area of dead space in the patient interface 3000 at the mask 3110, e.g., within the plenum chamber 3118. The presence of this dead space 3122 may result from the position of the exchanger 3120 such that the inspiratory flow path ends upstream of the plenum chamber 3118 and the expiratory flow path 3107 begins downstream of the plenum chamber 3118. The plenum chamber in this case is not a part of the inspiratory flow path or the expiratory flow path. Neither is the plenum chamber in the cross-flow between the inspiratory and the expiratory flow, as the inspiratory flow can circumvent the plenum chamber and be directed to the expiratory path without passing through the plenum chamber. In this case, the volume of the plenum chamber 3118 may represent the volume of the dead space 3122.

FIG. 11 shows a further example of the present technology, wherein the volume of the dead space 3122 is reduced or eliminated by extending the exchanger 3120 into the plenum chamber 3118. According to this example, the exchanger 3120 may be positioned so that it extends near or adjacent to the end of the plenum chamber 3118, which is distant from the exchanger 3120 (in FIG. 11 this distal end is rightmost side of the plenum chamber 3118). Locating the exchanger 3120 so that it extends near the distal end of the plenum chamber 3118, means that any remaining space of the plenum chamber is now on the path of the substantially uni-directional inflow of pressurized, breathable gas from the flow generator. Because the remaining space is directly on the flow path, it is well ventilated as the inspiratory and the expiratory flow can no longer intermingle substantially. As a result, the patient is no longer subjected to rebreathing of exhalate. Moreover, by positioning the heat and/or moisture exchange surface of the exchanger 3120 as close to the source of exhalate (e.g., the patient's airways via the seal-forming structure) as possible, the recovery of heat and/or moisture may be maximized. Also, due to the positioning the exchanger 3120 within the plenum chamber 3118 and/or near the seal-forming structure 3116, a more compact patient interface 3000 may be provided, thereby causing less interference for the patient's vision and making for a more aesthetically pleasing appearance.

It should be understood that the example in FIG. 11 is indicative of the general approach taken in order to reduce the dead space in the mask 3110 in the illustrated folded-back path configuration (in which the inspiratory path is transferred into an expiratory path that extends along and in the opposite direction of the inspiratory path). In this context, it is not essential whether the element extending closely to the further end of the plenum chamber 3118 is a moisture and/or heat exchanger 3120 or simply a tube of any (preferably cylindrical) shape, as long as the tube provides a cross-flow in the overlapping region between the inspiratory and expiratory paths and, thus, eliminates or reduces the mask's dead space. The tube may be impermeable for gas and moisture.

In FIG. 11, the exchanger 3120 is shown spaced away from the rightmost side of the plenum chamber 3118 such that the exhalate can enter the expiratory flow path 3107 unimpeded. In other words, exhalate need not pass directly through the exchanger 3120 to be discharged out the expiratory flow path 3107. Alternatively, the exchanger 3120 may be abutted against the plenum chamber 3118. In such an example, exhalate may be forced to pass through the exchanger 3120 to be discharged via the expiratory flow path 3107. In this example (not shown), the exchanger 3120 must be made from a gas permeable material so that the exhalate can pass therethrough. In the example shown in FIG. 11, it may not be necessary for the exchanger 3120 to be made from a gas permeable material because the exhalate can flow around the exchanger and into the expiratory flow path 3107.

FIGS. 12a and 12b show two indicated cross-sectional views of the conduit 4170 from FIG. 10. These views depict the coaxial arrangement of the inlet limb 3104 and the outlet limb 3106. FIG. 12a shows a cross-section taken through the conduit 4170 at the location of the exchanger 3120. FIG. 12b shows a cross-section taken through a portion of the conduit 4170 beyond the length of the exchanger 3120, where the inlet limb 3104 and the outlet limb 3106 are adjacent and coaxial. The cross-section of FIG. 12a may also be applicable to the example shown in FIG. 11. However, the cross-section would be taken near the seal-forming structure 3116 as the exchanger 3120 would be positioned adjacent thereto.

Also, the coaxial arrangement shown in FIGS. 10, 11, 12a, and 12b, where the expiratory flow path 3107 is internal to the inspiratory flow path 3105, may help reduce rainout (i.e., condensation of moisture) in the expiratory limb 3104. This rainout reduction may result from the outward and/or radial radiation of heat from expiratory flow path 3107 to the inspiratory flow path. In an alternative arrangement (not shown), the locations of the paths are exchanged and the expiratory flow path 3107 is external to the inspiratory flow path 3105. This will result in a reduced reduce rainout in the inspiratory limb as the (possibly) heated and humidified inspiratory path will be shielded from atmosphere by a jacket of gas at exhaled temperature and humidity.

While these examples have been depicted with the inspiratory flow path 3105 being external to the expiratory flow path 3107, it should be understood that this arrangement could be reversed such that it is the inspiratory flow path 3105 that is internal to the expiratory flow path 3107. Also, these examples have depicted a coaxial arrangement of the inlet limb 3104 and the outlet limb 3106, however, it should be understood that the conduit 4170 could be constructed in other arrangements, e.g., where inlet limb 3104 occupies one side of the conduit and the outlet limb 3106 occupies the other, adjacent side, while both limbs share a common internal wall therebetween. FIGS. 12c and 12d depict examples where the inspiratory flow path 3105 and the expiratory flow path 3107 are positioned adjacent and parallel to one another within the conduit 4170, rather than coaxially.

Also, it should be understood that in any of the examples of the present technology, shared or common walls of the inlet limb 3104 and the outlet 3106 may be formed from a heat conductive material and/or a moisture permeable material that is not gas permeable. This may allow for greater transfer of heat and/or moisture from the expiratory flow path 3107 to the inspiratory flow path.

It should also be understood that in any of the examples shown in FIGS. 12*a* to 12*d*, that the inlet limb 3104 and the outlet limb 3106 may be contained within a common external wall of the conduit 4170. In other words, when the patient is receiving therapy only one conduit 4170 may be used to connect the patient interface 3000 to the flow generator 4000 for the purpose of providing the flow of gas via the inspiratory flow path 3105 and removing the exhalate via the expiratory flow path 3107.

The conduit 4170, according to examples of the present technology, may also be insulated around its exterior. The external surface of the conduit 4170 may be made from a material that conducts little heat or an insulating sleeve or cover may provided to the exterior of the conduit 4170. Insulating the conduit 4170 in these ways may further reduce rainout (i.e., condensation of moisture) in the inspiratory flow path 3105. Also, heat losses to atmosphere may be reduced to better control the temperature of the gas provided to the patient's airways.

The conduit 4170, according to examples of the present technology, may also be heated to prevent rainout in the inspiratory flow path 3105. Wires may be provided to the conduit 4170 that heat the gas travelling to the patient in the inspiratory flow path 3105 by electrical resistance heating, for example. The heating function may be controlled by the control system of the flow generator 4000 or the humidifier 5000.

Even though the patient interface 3000 and the conduit 4170 are shown in the drawings as an integral device, the two components mat be completely separate, each of them having the indicated structure and being arranged for coupling with the other. For instance, the patient interface 3000 may be a standard patient interface, as indicated in FIG. 10 and be arranged for coupling at one end to a conduit 4170 having the structure indicated in FIG. 10. The conduit in this case may include the entire structure of the exchanger 3120. The coupling end of the patient interface 3000 in this case is chosen to be on the side of the mask. As a result, the direction of the incoming and outgoing flows is substantially parallel to the patient's face. In addition, the conduit 4170 may extend to the side of patient's head, providing the patient with additional options in handling the conduit.

In the case illustrated in FIG. 11, the patient interface 3000 may comprise the structure of the exchanger 3120 and be arranged for coupling with the conduit 4170, which in this case will comprise the coaxially arranged inlet and outlet structure for conducting the inspiratory and expiratory flow paths 3105, 3107. Whilst the exchanger 3120 is shown to extend through the entire width of the patient interface 3000, this does not have to be the case, and the exchanger 3120 may be sized to extend only for a portion of the width of the patient interface 3000.

5.5 Glossary

In certain forms of the present technology, one or more of the following definitions may apply. In other forms of the present technology, alternative definitions may apply.

5.5.1 General

Air: Air will be taken to include breathable gases, for example air with supplemental oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

5.5.2 Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO2), partial pressure of carbon dioxide (PCO2), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

5.5.3 Aspects of a Patient Interface

Functional dead space: The functional dead space refers to at least one region within a breathing circuit where a patient's exhalate may collect such that the normal flow of gas within the breathing circuit cannot effectively flush the exhalate from the breathing circuit.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

5.6 Other Remarks

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

It must be noted that as used herein and in the appended claims, the singular forms "a", "an", and "the" include their plural equivalents, unless the context clearly dictates otherwise.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

6 REFERENCE NUMERAL LIST

| | |
|---|---|
| mechanical ventilator | 10 |
| control line | 12 |
| supply conduit | 14 |
| expiratory valve | 16 |
| mask | 18 |
| mechanical ventilator | 20 |
| return conduit | 22 |
| supply conduit | 24 |
| mask | 28 |
| patient | 1000 |
| Bed partner | 1100 |
| patient interface | 3000 |
| positioning and stabilising structure | 3102 |
| inlet limb | 3104 |
| inspiratory flow path | 3105 |
| outlet limb | 3106 |
| expiratory flow path | 3107 |
| controllable valve | 3108 |
| mask | 3110 |
| inspiratory port | 3112 |
| expiratory port | 3114 |
| seal-forming structure | 3116 |
| plenum chamber | 3118 |
| exchanger | 3120 |
| dead space | 3122 |
| flow generator | 4000 |
| conduit | 4170 |
| humidifier | 5000 |

The invention claimed is:

1. A patient interface system for delivering pressurized gas to a patient, the patient interface system comprising:
    a patient interface including a plenum chamber, a seal-forming structure connected to the plenum chamber and configured to form a seal with the patient's face in use, the plenum chamber having an inspiratory port and an expiratory port located on generally opposite sides of the plenum chamber such that, in use, the inspiratory port and the expiratory port are positioned on generally opposite sides the patient's nose, and the plenum chamber configured to receive the patient's nose in use and to deliver the pressurized gas to the patient's airways, wherein said inspiratory port and said expiratory port are at least one of sized, oriented, positioned, and spaced apart to allow a cross-flow of pressurized gas to flow, in use, unidirectionally from the inspiratory port into the plenum chamber, to an entrance to the patient's airways, and out of the plenum chamber through the expiratory port to minimize dead space within the patient interface; and
    an outlet limb connected to the expiratory port, said outlet limb having an aperture in pneumatic communication with the plenum chamber, said aperture having an aperture size that is variable between a first configuration that is open and at least one second configuration that is different from the first configuration.

2. The patient interface system of claim 1, wherein the outlet limb comprises a controllable valve configured to be controlled by a controller.

3. The patient interface system of claim 2, wherein the controllable valve is adapted to release pressurized gas from the outlet limb through the aperture to atmosphere in the first configuration.

4. The patient interface system of claim 2, wherein the controllable valve is adapted to prevent a release of pressurized gas from the outlet limb through the aperture to atmosphere in the second configuration.

5. The patient interface system of claim 1, wherein the patient interface defines a substantially pneumatically unobstructed path from the inspiratory port, through the plenum chamber and to the expiratory port.

6. The patient interface system of claim 5, wherein the substantially pneumatically unobstructed path is substantially linear.

7. The patient interface system of claim 1, wherein the patient interface system is arranged for delivering pressurized gas to a pediatric patient.

8. The patient interface system of claim 1, further comprising:
headgear to removably attach the patient interface to the face of the patient.

9. The patient interface system of claim 1, wherein the seal-forming structure is a cushion adapted to contact the skin of the patient.

10. The patient interface system of claim 1, wherein the patient interface comprises a nasal mask.

11. The patient interface system of claim 1, wherein the patient interface comprises a full-face mask.

12. The patient interface system of claim 1, further comprising:
an inlet limb having a first end connected to the inspiratory port and adapted to connect to a flow generator at a second end.

13. The patient interface system of claim 1, wherein the inspiratory port and the expiratory port are substantially coaxial.

14. The patient interface system of claim 1, wherein the patient interface comprises a non-vented patient interface.

15. The patient interface system of claim 1, wherein the inspiratory port and the expiratory port are disposed on the patient interface such that there is substantially no backflow through the inspiratory port.

16. A ventilation system for providing breathable gas to a patient, the ventilation system comprising:
the patient interface system of claim 1;
a flow generator to generate a flow of pressurized, breathable gas to the patient; and
a controller to control the flow generator.

17. The ventilation system of claim 16, further comprising an inlet limb pneumatically connected to the flow generator and the inspiratory port of the patient interface.

18. A patient interface system for delivering pressurized gas to a patient, the patient interface system comprising:
a patient interface including a plenum chamber and a seal-forming structure connected to the plenum chamber and configured to form a seal with the patient's face in use, and the plenum chamber configured to receive the patient's nose in use and to deliver the pressurized gas to the patient's airways;
an inspiratory flow path connected to a first side of the plenum chamber; and
an expiratory flow path connected to a second side of the plenum chamber, said second side such that, in use, the inspiratory flow path and the expiratory flow path are positioned on generally opposite sides the patient's nose being disposed generally opposite the first side, the expiratory flow path having an opening disposed at a distance from the plenum chamber, said opening having an opening size that is variable between a first open configuration and at least one second configuration that is different from the first open configuration,
wherein the inspiratory flow path and the expiratory flow path are connected to the plenum chamber such that, in use, the pressurized gas flows from the inspiratory flow path into the plenum chamber, to an entrance to the patient's airways, and out of the plenum chamber through the expiratory flow path along a unidirectional flow path to minimize dead space within the patient interface.

19. The patient interface system of claim 18, wherein the unidirectional flow path is a substantially linear path.

20. The patient interface system of claim 18, wherein the patient interface system is arranged for delivering pressurized gas to a pediatric patient.

21. The patient interface system of claim 18, wherein the seal-forming structure is a cushion adapted to contact the face of the patient.

22. The patient interface system of claim 18, further comprising:
headgear adapted to secure the patient interface system to the patient.

23. The patient interface system of claim 18, wherein said inspiratory flow path comprises an inlet limb and said expiratory flow path comprises an outlet limb, and
wherein said inlet limb and said outlet limb are at least one of sized, oriented, positioned, and spaced apart to allow a cross-flow of pressurized gas to flow through the plenum chamber.

24. The patient interface system of claim 18, wherein the patient interface forms a substantially pneumatically unobstructed path from the inspiratory flow path to the expiratory flow path.

25. The patient interface system of claim 18, wherein the inspiratory flow path and the expiratory flow path are in pneumatic communication such that there is substantially no backflow through the inspiratory flow path.

26. The patient interface system of claim 18, wherein the patient interface comprises a nasal mask.

27. The patient interface system of claim 18, wherein the patient interface comprises a full-face mask.

28. The patient interface system of claim 18, wherein the patient interface comprises a non-vented patient interface.

* * * * *